United States Patent
Heuer et al.

(10) Patent No.: US 6,368,731 B2
(45) Date of Patent: *Apr. 9, 2002

(54) ELECTROLUMINESCENT ASSEMBLIES USING BORON CHELATES OF 8-AMINOQUINOLINE DERIVATIVES

(75) Inventors: Helmut-Werner Heuer; Rolf Wehrmann, both of Krefeld; Andreas Elschner, Mülheim, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/345,253

(22) Filed: Jun. 30, 1999

(30) Foreign Application Priority Data

Jul. 4, 1998 (DE) ........................................ 198 29 949

(51) Int. Cl.$^7$ .............................................. H05B 33/14
(52) U.S. Cl. ...................... 428/690; 428/691; 428/704; 428/917; 313/503; 313/504; 313/506; 313/507; 313/498
(58) Field of Search ................................ 428/690, 691, 428/917, 704; 313/503, 504, 506, 507, 498

(56) References Cited

U.S. PATENT DOCUMENTS

| | | | |
|---|---|---|---|
| 4,539,507 A | 9/1985 | VanSlyke et al. | 313/504 |
| 4,769,292 A | 9/1988 | Tang et al. | 428/690 |
| 4,923,774 A | 5/1990 | Van der Auweraer et al. | 430/59 |
| 4,959,430 A | 9/1990 | Jonas et al. | 526/257 |
| 4,987,042 A | 1/1991 | Jonas et al. | 429/213 |
| 5,077,142 A | 12/1991 | Sakon et al. | 428/690 |
| 5,154,769 A | 10/1992 | Kuske et al. | 106/459 |
| 5,164,005 A | 11/1992 | Kuske et al. | 106/459 |
| 5,300,575 A | 4/1994 | Jonas et al. | 525/186 |
| 5,484,922 A * | 1/1996 | Moore et al. | 546/7 |
| 5,554,450 A * | 9/1996 | Shi et al. | 428/690 |
| 5,681,664 A * | 10/1997 | Tamano et al. | 428/690 |
| 5,766,515 A | 6/1998 | Jonas et al. | 252/500 |
| 5,965,281 A * | 10/1999 | Cao | 428/690 |

FOREIGN PATENT DOCUMENTS

| | | |
|---|---|---|
| DE | 4211459 | 10/1993 |
| EP | 0 278 757 | 8/1988 |
| EP | 0 278 758 | 8/1988 |
| EP | 0 294 061 | 12/1988 |
| EP | 0 443 861 | 8/1991 |
| EP | 0 532 798 | 3/1993 |
| EP | 0 579 151 | 1/1994 |
| EP | 0 406 762 | 9/1994 |
| WO | 90/13148 | 11/1990 |
| WO | 92/03490 | 3/1992 |
| WO | 92/03491 | 3/1992 |
| WO | 92/16023 | 9/1992 |

OTHER PUBLICATIONS

Bayer's Product Information (Trial Product AI 4071, Sep., 1995).*

Hohaus, Eberhard et al: "Boron chelates and boron metal chelates with chelating agents Of the pyridine and quinoline series and their N–oxides" Chem. Ber. (1969), 102(12), 4025–31, XP002127342 *das ganze Dokument*.

Advanced Materials, G. Leising et al (month unavailable) 1992, No. 1, pp. 36–37, "Realization of a Blue–Light–Emitting Device using Poly(p–phenylene)".

Friend et al, J. Chem. Soc. Chem. Commun., 32, (month unavailable) 1992, pp. 32–34 "Synthesis of a Segmented Conjugated Polymer Chain Giving a Blue–shifted Electroluminescence and Improved Efficiency".

Saito et al, Polymer, Jun. 1990, pp. 1137–1141, vol. 31, "Polyarylenevinylene films prepared from precursor polymers soluble in organic solvents".

Friend et al, Physical Review B, vol. 42, No. 18, Dec. 15, 1990, pp. 11670–11681 "Photoexcited states in poly(p–phenylene vinylene): Comparison with trans, trans–distyrylbenze, a model oligomer".

M Stolka et al, Pure & Applied Chem. vol. 62, No. 1, (month unavailable) 1995, pp. 175–182 "Electroluminesence from single layer molecularly doped polymer films".

H. Bässler et al, Advanced Materials (month unavailable) 1995, 7, No. 6, pp. 551–554, Efficient Two Layer LEDs on a Polymer Blend Basis.

(List continued on next page.)

Primary Examiner—Cynthia H. Kelly
Assistant Examiner—Ling Xu
(74) Attorney, Agent, or Firm—Joseph C. Gil; Richard E. L. Henderson

(57) ABSTRACT

Electroluminescent assembly comprising a substrate, an anode, an electroluminescent element and a cathode, where at least one of the two electrodes is transparent in the visible spectral region and the electroluminescent element contains one or more zones selected from the group consisting of hole injection zone, hole transport zone, electroluminescent zone, electron transport zone and electron injection zone in the order specified, where each of the zones present may also assume functions of the other zones mentioned, characterized in that the electroluminescent element contains a boron complex of an 8-aminoquinoline derivative.

12 Claims, No Drawings

OTHER PUBLICATIONS

K. Nagai et al, Appl. Phys. Letter, 67(16) (month unavailable) 1995, pp. 2281–2283 "Single–layer white light–emitting organic electroluminescent devices based on dye–dispersed poly(N–vinylcarbazole)".

Naito et al, J. Phys. Chem., Feb., 1993, 97, pp. 6240–6248, "Molecular Design for Nonpolymeric Organic Dye Glasses with Thermal Stability: Relation between Thermodynamic Parameters and Amorphous Properties".

Adachi et al, Appl. Phys. Lett. 66(20, May 15, 1995, pp. 2679–2681, "Molecular design of hole transport material for obtaining high durability in organic electroluminescent diodes".

Hohaus et al, Chem. Ber. 102, (month unavailable) 1969, pp. 4025–4031, "Borchelate mit Chelatbildnern der Pyridin– und Chinolin–Reihe und ihren N–Oxiden".

Houben–Weyl Methoden der organischem Chemie, vol. E20, Markromolekulare Stoffe, Part 2, (month unavailable) 1987, pp. 1141–1143, Dr. Günter Schröder, "λ)von Acryl–Verbindungen".

Houben–Weyl, 4/IC, 14–102 (date unavailable), Prof. Dr. Zymalkowski, A. Katalystische Hydrierung.

\* cited by examiner

ELECTROLUMINESCENT ASSEMBLIES USING BORON CHELATES OF 8-AMINOQUINOLINE DERIVATIVES

An electroluminescent (EL) assembly is characterized in that it emits light and an electric current flows when an electric potential is applied. Such assemblies have long been known in industry under the name "light emitting diodes" (LEDs). The emission of light results from recombination of positive charges (holes) and negative charges (electrons) with emission of light.

In the development of light-emitting components for electronics or photoelectronics, use is at present made mainly of inorganic semiconductors such as gallium arsenide. Dot-shaped display elements can be produced on the basis of such substances. Large-area assemblies are not possible.

Apart from light emitting semiconductor diodes, electroluminescent assemblies based on vapour-deposited low molecular weight organic compounds are known (U.S. Pat. Nos. 4,539,507, 4,769,292, and 5,077,142, EP-A 0 406 762, EP-A 0 278 758, and EP-A 0 278 757).

Furthermore, polymers such as poly-(p-phenylenes) and poly-(p-phenylene-vinylenes) (PPVs) have been described as electroluminescent polymers: G. Leising et al., Adv. Mater. 4 (1992) No. 1; Friend et al., J. Chem. Soc., Chem. Commun. 32 (1992); Saito et al., Polymer, 1990, Vol. 31, 1137; Friend et al., Physical Review B, Vol. 42, No. 18, 11670 or WO 90/13148. Further examples of PPV in electroluminescent displays are described in EP-A 0 443 861, WO-A 92/03490 and 92/03491.

EP-A 0 294 061 discloses an optical modulator based on polyacetylene.

To produce flexible polymer LEDs, Heeger et al. have proposed soluble, conjugated PPV derivatives (WO-A 92/16023).

Polymer blends of different compositions are likewise known: M. Stolka et al., Pure & Appt. Chem., Vol. 67, No. 1, pp 175–182, 1995; H. Bässler et al., Adv. Mater. 1995, 7, No. 6, 551; K. Nagai et al., Appl. Phys. Lett. 67 (16), 1995, 2281; EP-A 0 532 798.

The organic EL assemblies generally contain one or more layers comprising organic charge transport compounds. The in-principle structure in the order of the layers is as follows:

1. Support, substrate
2. Base electrode
3. Hole injection layer
4. Hole transport layer
5. Light-emitting layer
6. Electron transport layer
7. Electron injection layer
8. Top electrode
9. Contacts
10. Covering, encapsulation.

Layers 3 to 7 represent the electroluminescent element.

This structure represents the most general case and can be simplified by leaving out individual layers so that one layer assumes a plurality of functions. In the simplest case, the EL assembly comprises two electrodes between which there is located one organic layer which fulfils all functions, including the emission of light. Such systems are described, for example, in the Application WO-A 90/13148 on the basis of poly(p-phenylene-vinylene).

Multilayer systems can be built up by means of vapour deposition processes in which the layers are applied successively from the gas phase or by means of casting processes. Owing to the higher process speeds, casting processes are preferred. However, partial dissolution of a layer which has already been applied when the next layer is applied on top of it can in certain cases be a difficulty.

It is an object of the present invention to provide electroluminescent assemblies having a high light flux, in which novel boron complexes or chelates having improved solubility in customary solvents are to be used as emitters and/or electron conductors. These novel boron complexes should also be able to be applied from the gas phase by means of vapour deposition processes.

It has been found that electroluminescent assemblies containing the boron complexes mentioned below meet these requirements. In the following, the term "zone" is equivalent to the term "layer".

The present invention accordingly provides electroluminescent assemblies comprising a substrate, an anode, an electroluminescent element and a cathode, where at least one of the two electrodes is transparent in the visible spectral region and the electroluminescent element contains one or more zones selected from the group consisting of hole injection zone, hole transport zone, electroluminescent zone, electron transport zone and electron injection zone in the order specified, where each of the zones present may also assume functions of the other zones mentioned, characterized in that the electroluminescent element contains a boron complex of 8-aminoquinoline derivatives.

The hole injection zone preferably contains an uncharged or cationic polythiophene of the formula (I)

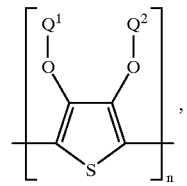

(I)

where

Q$^1$ and Q$^2$ represent, independently of one another, hydrogen, substituted or unsubstituted (C$_1$–C$_{20}$)-alkyl, CH$_2$OH or (C$_6$–C$_{14}$)-aryl or Q$^1$ and Q$^2$ together represent —(CH$_2$)$_m$—CH$_2$— where m=0 to 12, preferably 1 to 5, (C$_6$–C$_{14}$)-arylene, and n represents an integer from 2 to 10,000, preferably from 5 to 5000.

The hole conduction zone adjoining the hole injection zone preferably contains one or more aromatic tertiary amino compounds, preferably substituted or unsubstituted triphenylamine compounds, particularly preferably 1,3,5-tris(aminophenyl)benzene compounds of the formula (II).

The zone or zones located between the hole injection zone and the cathode can also assume a plurality of functions, i.e. one zone can contain, for example, hole-injecting, hole-transporting, electroluminescent, electron-transporting and/or electron-injecting substances.

The electroluminescent element can additionally contain one or more transparent polymeric binders.

The substituted or unsubstituted 1,3,5-tris(aminophenyl) benzene compound preferably represents an aromatic tertiary amino compound of the general formula (II)

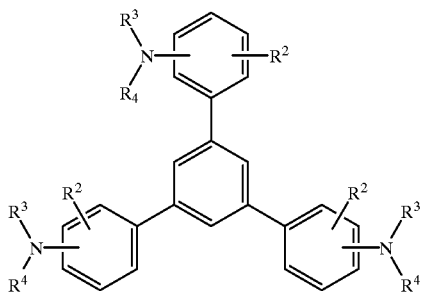
(II)

where

- $R^2$ represents hydrogen, substituted or unsubstituted alkyl or halogen,
- $R^3$ and $R^4$ represent, independently of one another, substituted or unsubstituted $(C_1-C_{10})$-alkyl, alkoxycarbonyl-substituted $(C_1-C_{10})$-alkyl, or substituted or unsubstituted aryl, aralkyl or cycloalkyl,
- $R^3$ and $R^4$ preferably represent, independently of one another, $(C_1-C_6)$-alkyl, in particular methyl, ethyl, n- or iso-propyl, n-, iso-, sec- or tert-butyl, $(C_1-C_4)$-alkoxycarbonyl-$(C_1-C_6)$-alkyl, for example methoxycarbonyl-,ethoxycarbonyl-, propoxycarbonyl- or butoxycarbonyl-$(C_1-C_4)$-alkyl or unsubstituted or $(C_1-C_4)$-alkyl- and/or $(C_1-C_4)$-alkoxy-substituted phenyl-$(C_1-C_4)$-alkyl, naphthyl-$(C_1-C_4)$alkyl, cyclopentyl, cyclohexyl, phenyl or naphthyl.

Particularly preferably, $R^3$ and $R^4$ represent, independently of one another, unsubstituted phenyl or naphthyl or else phenyl or naphthyl substituted by from one to three methyl, ethyl, n-, iso-propyl, methoxy, ethoxy, n- and/or iso-propoxy radicals.

$R^2$ preferably represents hydrogen, $(C_1-C_6$-alkyl, for example methyl, ethyl, n- or iso-propyl, n-, iso-, sec- or tert-butyl, or chlorine.

Such compounds and their preparation are described in U.S. Pat. No. 4,923,774 for use in electrophotography; this patent is hereby expressly incorporated by reference into the present description. The tris-nitrophenyl compound can, for example, be converted into the tris-aminophenyl compound by generally known catalytic hydrogenation, for example in the presence of Raney nickel (Houben-Weyl 4/1C, 14–102. Ullmann (4) 13, 135–148). The amino compound is reacted with substituted halogenobenzenes in a generally known manner.

The following compounds may be mentioned by way of example:

A1
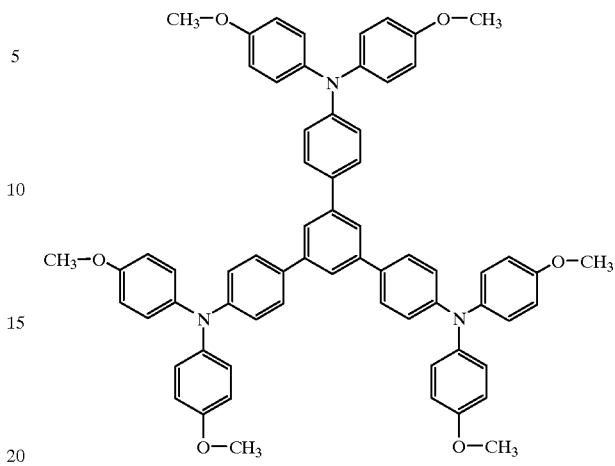

A2
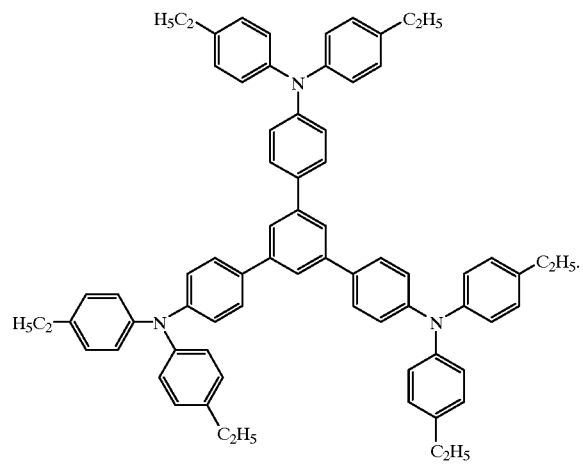

Apart from the tertiary amino compound, further hole conductors, e.g. in the form of a mixture with the tertiary amino compound, may also be used for building up the electroluminescent element. The further hole conductor or conductors can be, on the one hand, one or more compounds of the formula (II), including mixtures of isomers, or, on the other hand, mixtures of hole transport compounds with compounds of tertiary amino compounds having the general formula (II) and having various structures.

A listing of possible hole injection and hole conductor materials is given in EP-A 0 532 798.

In the case of mixtures of the aromatic amines, the compounds can be used in any ratio.

Examples which may be mentioned are:

Materials which have hole-conducting properties and can be used in pure form or as mixing partners for the tertiary amino compounds are, for example, the following compounds, where $X^1$ to $X^6$ represent, independently of one another H, halogen, alkyl, aryl, alkoxy, aryloxy.

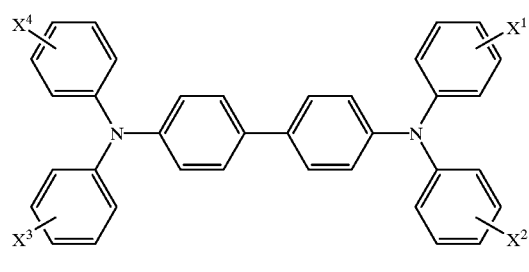
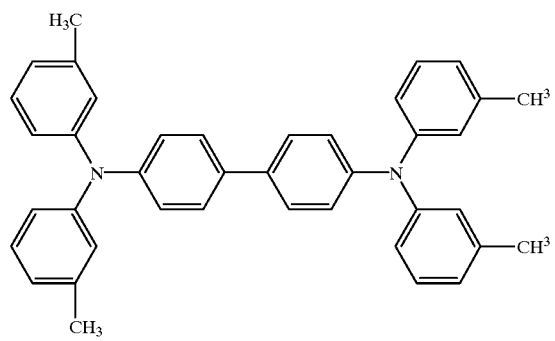
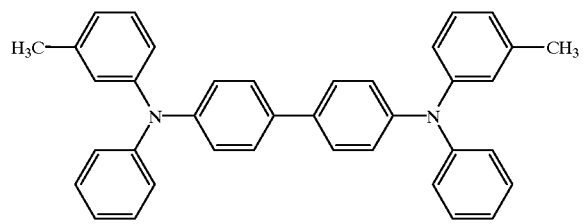
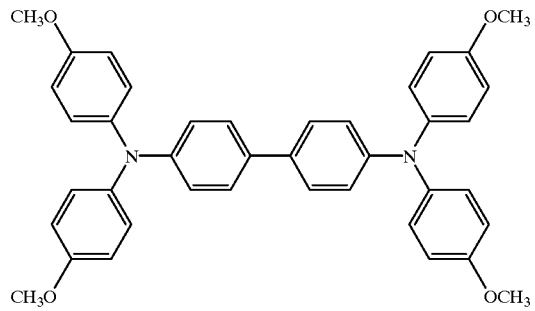
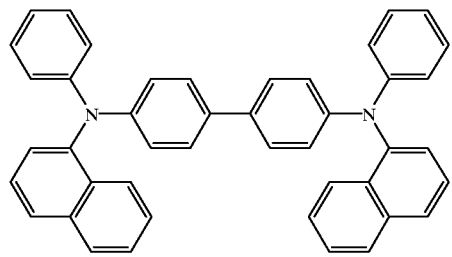
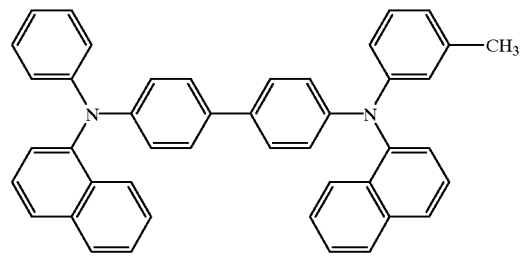
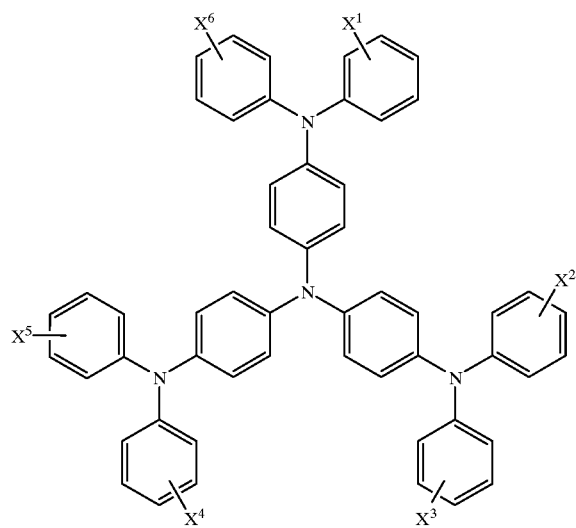
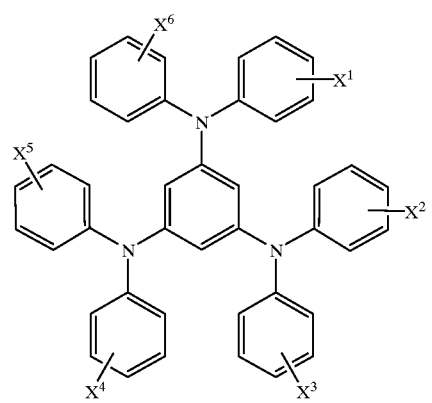

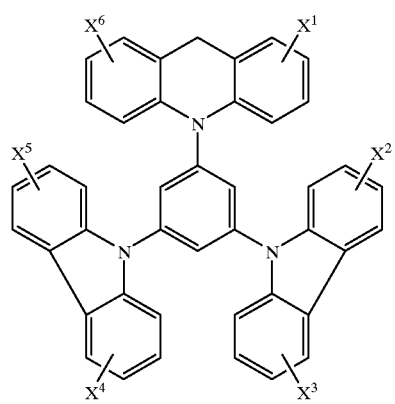
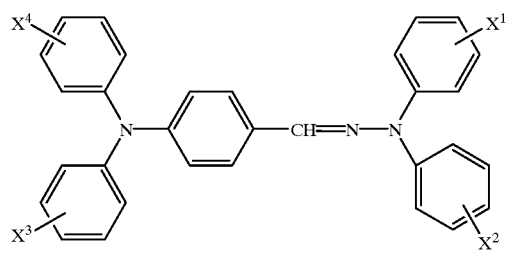
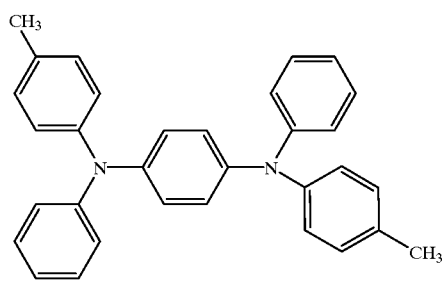
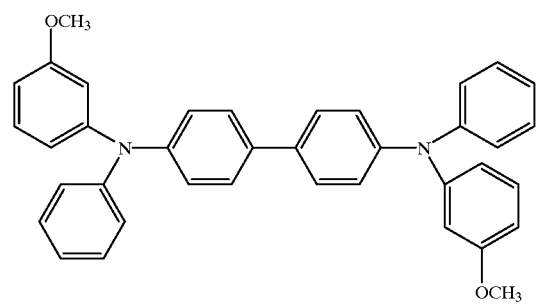
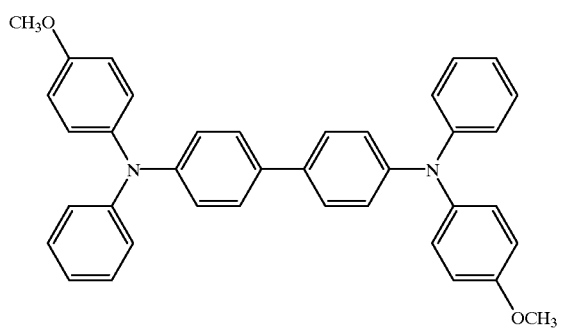
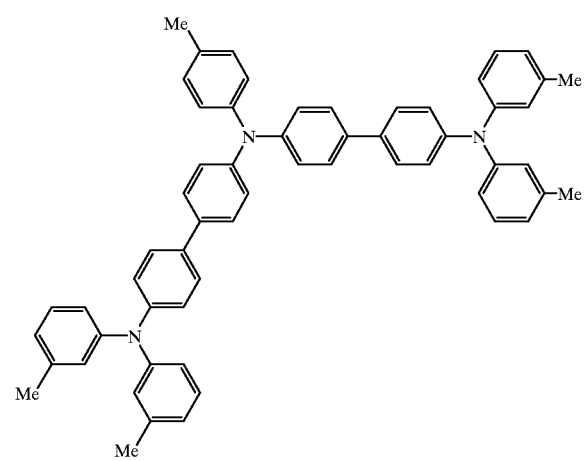
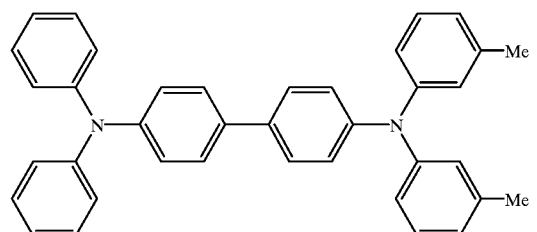
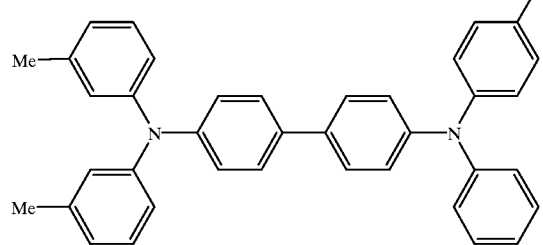

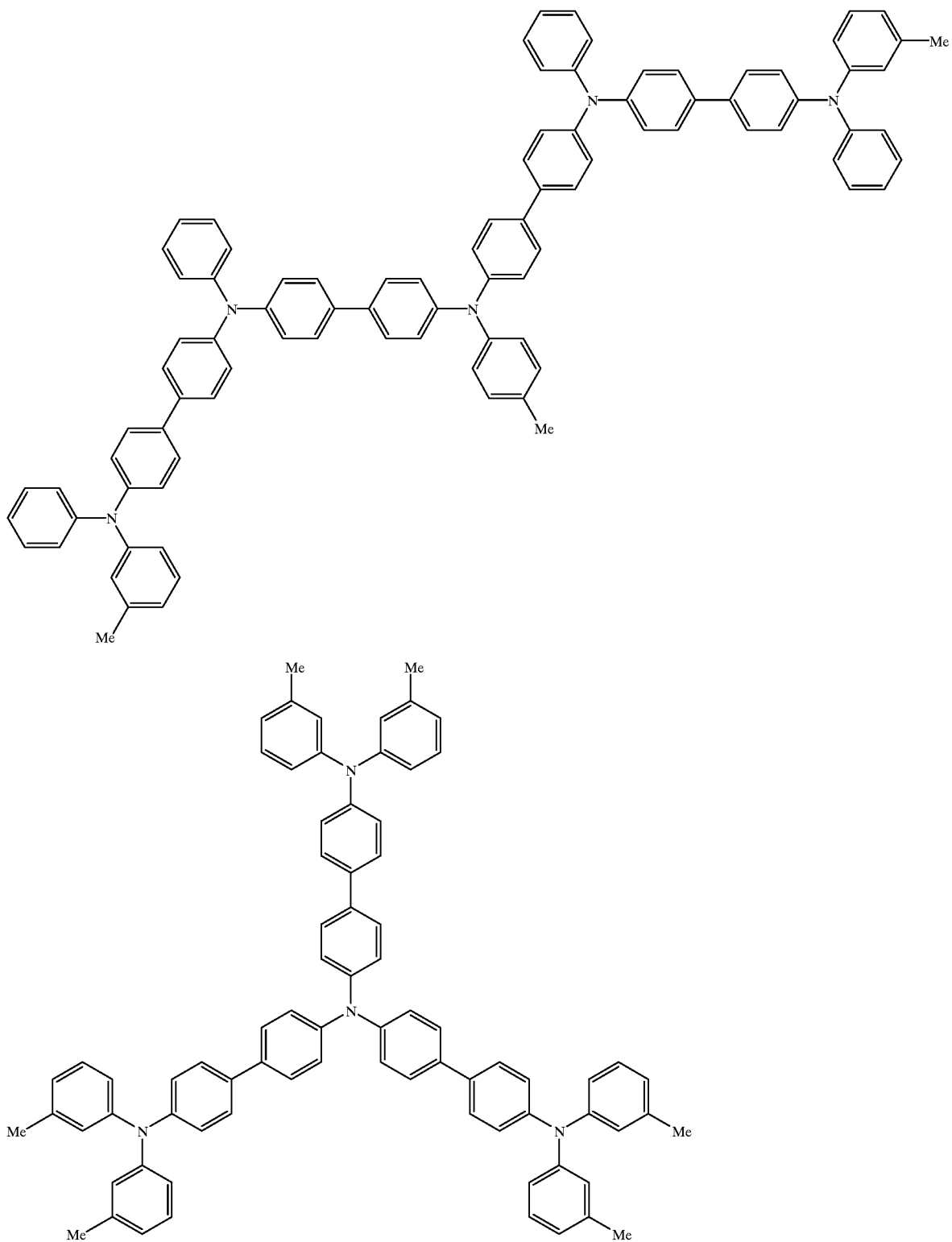
Me = methyl

These and further examples are described in J. Phys. Chem. 1993, 97, 6240–6248 and Appl. Phys. Lett., Vol. 66, No. 20, 2679–2681.

In general, various amines having different basic structures and/or different substitution patterns can be mixed. $X^1$ to $X^6$ preferably represent, independently of one another, hydrogen, fluorine, chlorine, bromine, $(C_1$–$C_{10})$-, in particular $(C_1$–$C_4)$-alkyl or -alkoxy, phenyl, naphthyl, phenoxy and/or naphthyloxy. The aromatic rings may be substituted by one, two, three or four, identical or different radicals $X^1$ to $X^6$.

The polythiophenes having the structural repeating unit of the formula (I) are known (cf. EP-A 0 440 958 and 0 339 340). The preparation of the dispersions or solutions used according to the invention is described in EP-A 0 440 957 and DE-A 42 11 459.

The polythiophenes in the dispersion or solution are preferably used in cationic form as are obtained, for example, by treatment of the neutral thiophenes with oxidizing agents. Customary oxidizing agents such as potassium peroxodisulphate are used for the oxidation. The oxidation gives the polythiophenes positive charges which are not in the formulae since their number and position cannot be determined unambiguously. They can be prepared directly on supports using the methods described in EP-A 0 339 340.

$Q^1$ and $Q^2$ in formula (I) are preferably —$(CH_2)_m$—$CH_2$— where $m=1$ to 4, very particularly preferably ethylene.

Preferred cationic or neutral polydioxythiophenes comprise structural units of the formula (Ia) or (Ib)

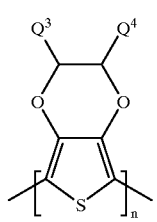

(Ia)

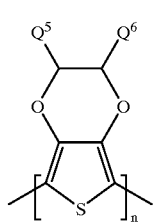

(Ib)

where $Q^3$ and $Q^4$ represent, independently of one another, hydrogen, substituted or unsubstituted $(C_1$–$C_{18})$-alkyl, preferably $(C_1$–$C_{10})$-, in particular $(C_1$–$C_6)$-alkyl, $(C_2$–$C_{12})$-alkenyl, preferably $(C_2$–$C_8)$-alkenyl, $(C_3$–$C_7)$-cycloalkyl, preferably cyclopentyl or cyclohexyl, $(C_7$–$C_{15})$-aralkyl, preferably phenyl-$(C_{1-4})$-alkyl, $(C_6$–$C_{10})$-aryl, preferably phenyl or naphthyl, $(C_1$–$C_{18})$-alkoxy, preferably $(C_1$–$C_{10})$-alkoxy, preferably methoxy, ethoxy, n- or iso-propoxy, or $(C_2$–$C_{18})$-alkyloxy ester and $Q^5$ and $Q^6$ represent, independently of one another, hydrogen or $(C_1$–$C_{18})$-alkyl, preferably $(C_1$–$C_{10})$-, in particular $(C_1$–$C_6)$-alkyl, $(C_2$–$C_{12})$-alkenyl, preferably $(C_2$–$C_8)$-alkenyl, $(C_3$–$C_7)$-cycloalkyl, preferably cyclopentyl or cyclohexyl, $(C_7$–$C_{15})$-aralkyl, preferably phenyl-$(C_1$–$C_4)$-alkyl, $(C_6$–$C_{10})$-aryl, preferably phenyl or naphthyl, $(C_1$–$C_{18})$-alkoxy, preferably $(C_1$–$C_{10})$-alkoxy, for example methoxy, ethoxy, n- or iso-propoxy, or $(C_2$–$C_{18})$-alkyloxy ester which are each substituted by at least one sulphonate group, where if $Q_5$ represents hydrogen, $Q^6$ is not hydrogen and vice versa, and n represents an integer from 2 to 10,000, preferably from 5 to 5000.

Particular preference is given to cationic or uncharged polythiophenes of the formulae (Ia-1) and (Ib-1)

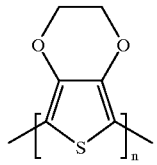

(Ia-1)

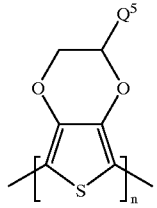

(Ib-1)

where $Q^5$ and n are as defined above.

To balance the positive charge, the cationic form of the polythiophenes contains anions, preferably polyanions.

Polyanions present are preferably the anions of polymeric carboxylic acids such as polyacrylic acids, polymethacrylic acid or polymaleic acids and polymeric sulphonic acids such as polystyrenesulphonic acids and polyvinylsulphonic acids. These polycarboxylic and polysulphonic acids can also be copolymers of vinylcarboxylic and vinylsulphonic acids with other polymerizable monomers such as acrylates and styrene.

The anion of polystyrenesulphonic acid is particularly preferred as counterion.

The molecular weight of the polyacids forming the polyanions is preferably from 1000 to 2,000,000, particularly preferably from 2000 to 500,000. The polyacids or their alkali metal salts are commercially available, e.g. polystyrenesulphonic acids and polyacrylic acids, or else can be prepared by known methods (see, for example, Houben-Weyl, Methoden der organischen Chemie, Volume E 20 Makromolekulare Stoffe, Part 2 (1987), p. 1141 ff.).

In place of the free polyacids required for the formation of the dispersions of polydioxythiophenes and polyanions, it is also possible to use mixtures of alkali metal salts of the polyacids and corresponding amounts of monoacids.

In the case of the formulae (Ib) and (Ib-1), the polydioxythiophenes bear positive and negative charges in the monomer unit itself.

The assemblies of the invention may, if desired, contain polymers and/or copolymers as binder, for example polycarbonates, polyester carbonates, copolymers of styrene such as SAN or styrene-acrylates, polysulphones, polymers based on vinyl-containing monomers such as poly(meth)acrylates, polyvinylpyrrolidone, polyvinylcarbazol, vinyl acetate and vinyl alcohol polymers and copolymers, polyolefins, cyclic olefin copolymers, phenoxy resins, etc. It is also possible to use mixtures of various polymers. The polymeric binders have molecular weights of from 10,000 to 2,000,000 g/mol, are soluble and film-forming and are transparent in the visible spectral region. They are described, for example, in Encyclopedia of Polymer Science and Engineering, 2nd ed., A. Wiley-Interscience publication. They are usually used in an amount of up to 95% by weight, preferably up to 80% by weight, based on the total weight of the electroluminescent elements.

The boron complex (boron chelate) is preferably a compound of the general formula (III)a or (III)b

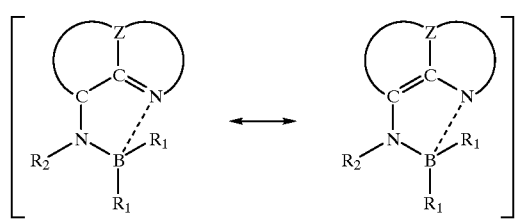

(III)a and

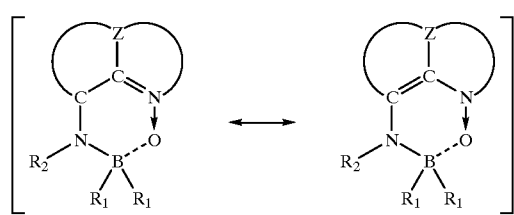

(III)b where $R_1$ represents a substituted or unsubstituted aryl radical or fluorine and $R_2$ represents a substituted or unsubstituted acyl or acyloxy radical or hydrogen and Z represents, independently in the two forms, atoms which complete a structure comprising at least 2 fused rings.

Particular preference is given to a compound of the general formula (IIIc) or (IIId)

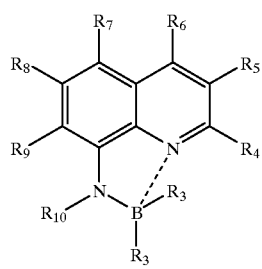

(III)c

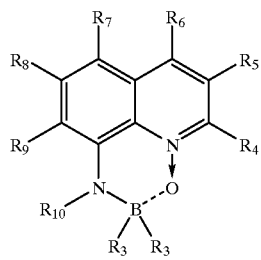

(III)d where $R_3$ represents substituted or unsubstituted ($C_6$–$C_{10}$)-aryl or halogen, $R_4$, $R_5$, $R_6$, $R_7$, $R_8$ and $R_9$ represent, independently of one another, hydrogen, substituted or unsubstituted ($C_1$–$C_{16}$)-alkyl or halogen or sulphonamido or cyano or a substituted or unsubstituted amino group, $R_{10}$ represents a substituted or unsubstituted acyl or acyloxy radical.

Very particular preference is given to a compound of the general formula (IIIe), (IIIf) or (IIIg)

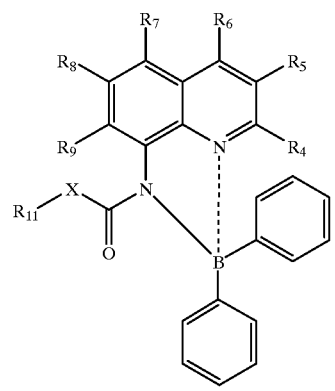

(III)e

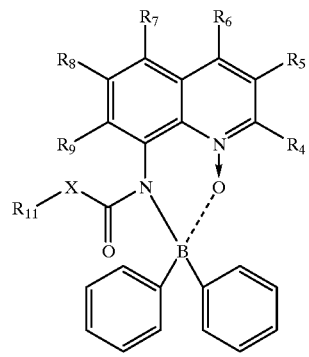

(III)f

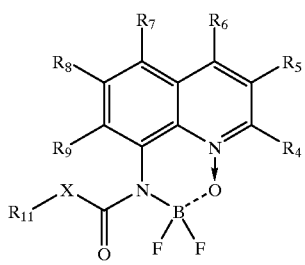

(III)g

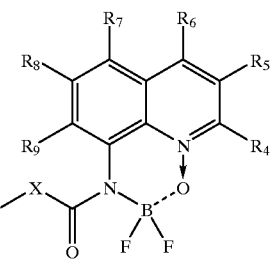

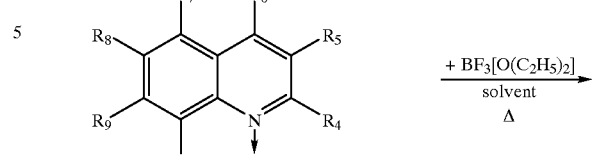

where

R$_4$, R$_5$, R$_6$, R$_7$, R$_8$ and R$_9$ represent, independently of one another, in particular hydrogen, branched or unbranched (C$_1$–C$_{12}$)-alkyl, for example methyl, ethyl or 4-ethyl-1-methyloctyl, or chlorine or a sulphonamido radical or cyano or a substituted amino group, R$_{11}$ represents branched or unbranched alkyl which may be unsubstituted or substituted, for example by an amino group, X represents an O atom or a group —CH$_2$— or —NH—.

Such compounds and their preparation are known as fluorescent compounds in chemical analysis and are described, for example, in E. Hohaus, F. Umland; Chem. Ber. 102. 4025–4031 (1969).

A general synthesis scheme which differs only in the choice of solvent is:

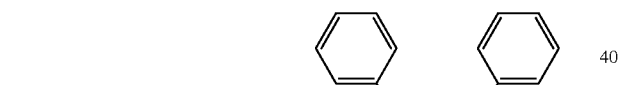

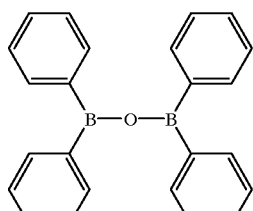

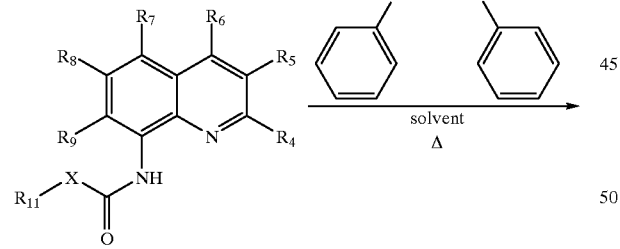

Examples are the following compounds:

B1)

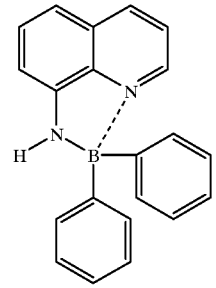

B2)

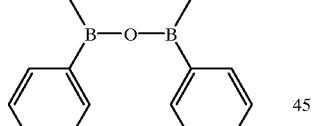

B3)

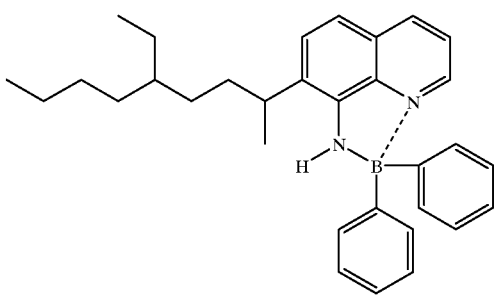

B4) 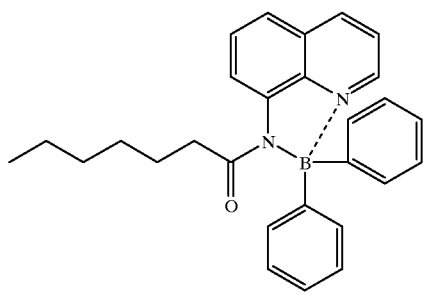
B5) 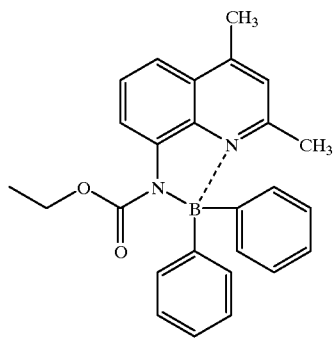
B6) 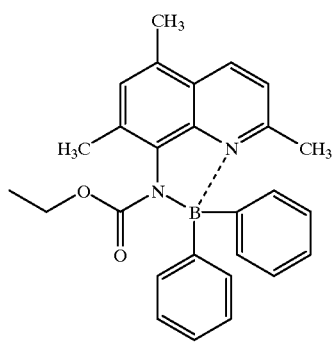
B7) 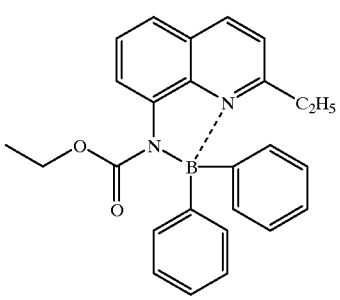
B8) 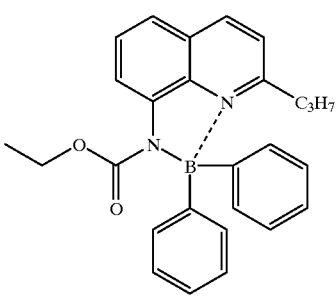
B9) 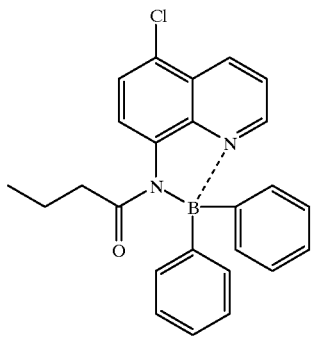
B10) 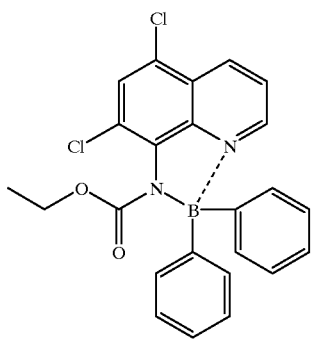
B11) 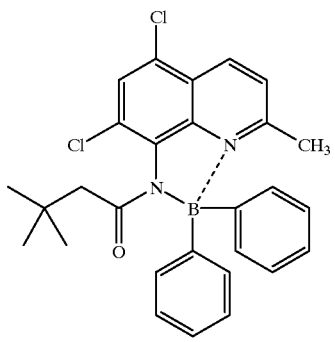
B12) 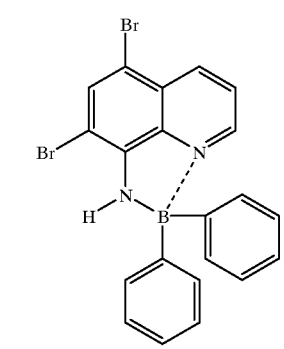

B13) 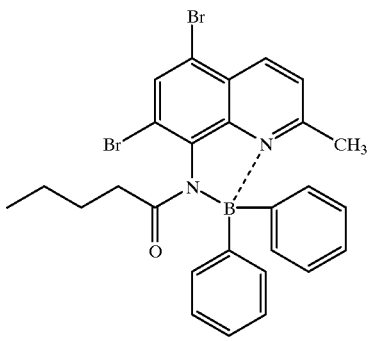

B14) 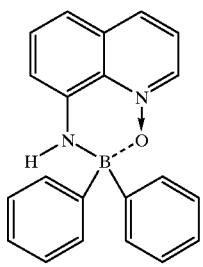

B15) 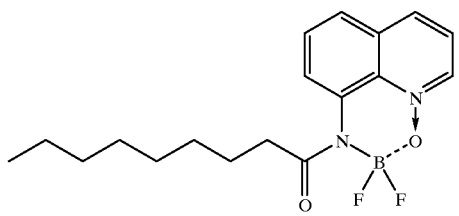

B16) 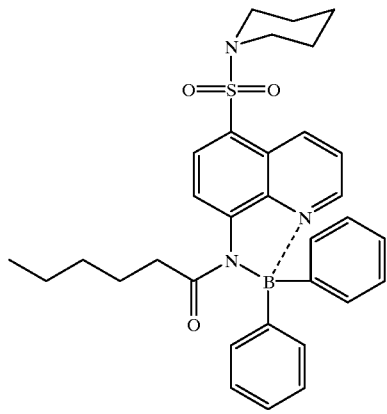

B17) 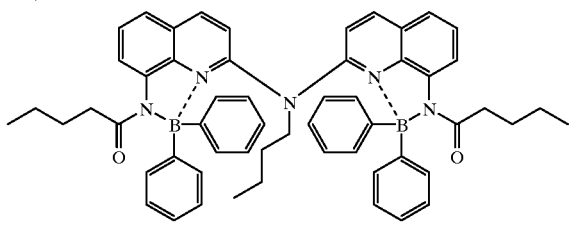

B18) 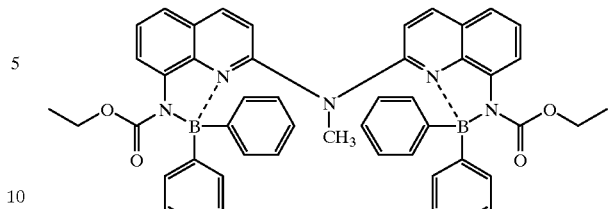

B19) 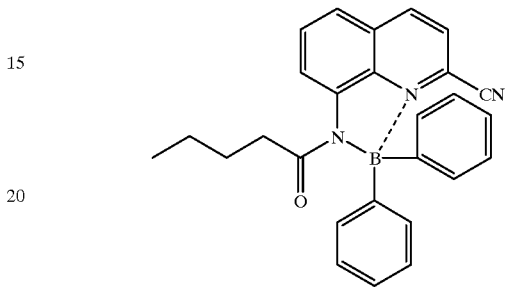

B20) 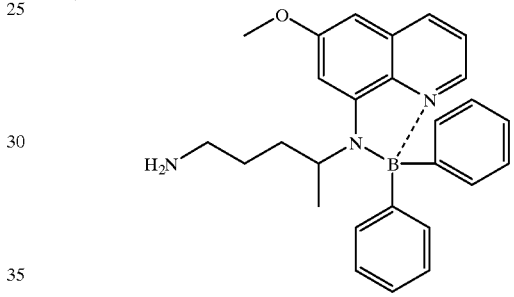

B21) 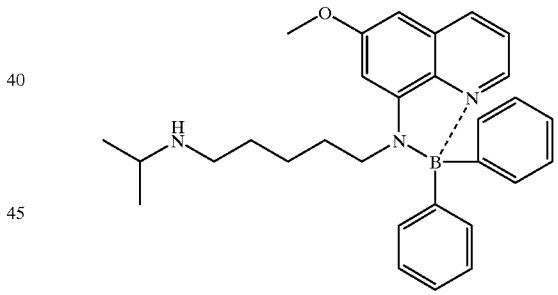

It is possible to use one or more compounds of the formulae B1 to B2 1.

The 8-aminoquinoline ligands can be prepared by known methods of organic chemistry.

To produce the electroluminescent element, the boron complex and, if desired, the tertiary amino compound and the binder are dissolved in a suitable solvent and applied to a suitable substrate by casting, doctor blade coating or spin coating. However, if desired, the boron complex can also be applied separately as a layer by a vapour deposition process. The substrate can be, for example, glass or a polymer material which is provided with a transparent electrode. As polymer material, it is possible to use, for example, a film of polycarbonate, polyester such as polyethylene terephthalate or polyethylene naphthalate, polysulphone or polyimide.

Suitable transparent electrodes are
a) metal oxides, e.g. indium-tin oxide (ITO), tin oxide (NESA), zinc oxide, doped tin oxide, doped zinc oxide, etc.,
b) semi-transparent metal films, e.g. Au, Pt, Ag, Cu etc.,
c) conductive polymer films such as polyanilines, polythiophenes, etc.

The metal oxide electrodes and the semitransparent metal film electrodes are applied in a thin layer by techniques such as vapour deposition, sputtering, platination, etc. The conductive polymer films are applied from the solution by techniques such as spin coating, casting, doctor blade coating, etc.

The thickness of the transparent electrode is from 3 μm to several μm, preferably from 10 nm to 500 nm.

The electroluminescent layer is applied as a thin film directly to the transparent electrode or to a charge transport layer which may be present. The thickness of the film is from 10 to 500 nm, preferably from 20 to 400 nm, particularly preferably from 50 to 250 nm.

A further charge transport layer may be inserted on the electroluminescent layer before application of a counterelectrode.

A listing of suitable intermediate charge transport layers, which may be hole conductor or electron conductor materials and may be present in polymeric or low molecular weight form, if desired as a blend, is given in EP-A 0 532 798. Particularly suitable charge transport materials are specifically substituted polythiophenes which have hole transport properties. They are described, for example, in EP-A 0 686 662.

The content of a low molecular weight hole conductor in a polymeric binder can be varied within the range from 2 to 97% by weight; the content is preferably from 5 to 95% by weight, particularly preferably from 10 to 90% by weight, in particular from 10 to 85% by weight. The hole injection or hole conduction zones can be deposited by various methods.

Film-forming hole conductors can also be used in pure form (100% hole conductor). If desired, the hole injection or hole conduction zone can also contain amounts of an electroluminescent substance.

Blends consisting entirely of low molecular weight compounds can be vapour-deposited; soluble and film-forming blends, which may contain a binder in addition to low molecular weight compounds, can be deposited from solution, e.g. by means of spin coating, casting or doctor blade coating.

It is also possible to apply emitting and/or electron-conducting substances in a separate layer on the hole conduction layer. Here, an emitting substance can also be added as dopant to the layer containing the compound (II) and, in addition, an electron-conducting substance can be applied. An electroluminescent substance can also be added to the electron injection or electron conduction layer.

The content of low molecular weight electron conductors in the polymeric binder can be varied within the range from 2 to 95% by weight; the content is preferably from 5 to 90% by weight, particularly preferably from 10 to 85% by weight. Film-forming electron conductors can also be used in pure form (100% electron conductor).

The counterelectrode comprises a conductive substance which may be transparent. Preference is given to metals, e.g. Al, Au, Ag, Mg, In, etc., or alloys and oxides of these, which can be applied by techniques such as vapour deposition, sputtering or platination.

The assembly of the invention is connected to a power source by means of two electric leads (e.g. metal wires) connected to the two electrodes.

On application of a DC potential in the range from 0.1 to 100 volt, the assemblies emit light having a wavelength of from 200 to 2000 nm. They display photoluminescence in the range from 200 to 2000 nm.

The assemblies of the invention are suitable for producing lighting units and units for the display of information.

EXAMPLES

Example 1

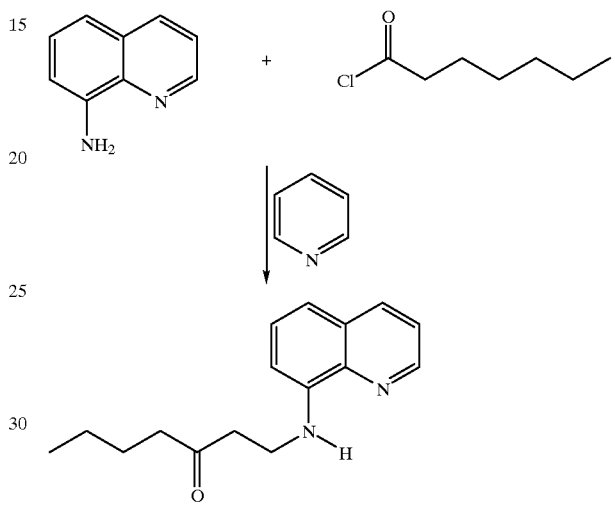

5.0 g (34.67 mmol) of 8-arminoquinoline together with 50 ml of dry pyridine are placed in the reaction vessel. while cooling in an ice bath, 5.15 g (34.67 mmol) of heptanoyl chloride are added dropwise. The mixture is subsequently stirred for 6 hours at room temperature. The reaction mixture is then poured into 500 ml of ice water. The aqueous solution is shaken with portions of chloroform, using a total of 600 ml of chloroform. The organic phase is dried over sodium sulphate.

Removal of the solvent and distillation under a high vacuum gave 6.69 g (≃75.3% of theory) of the desired ligand.

Example 2

Complexation

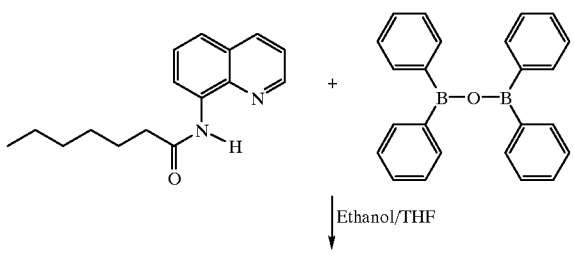

-continued

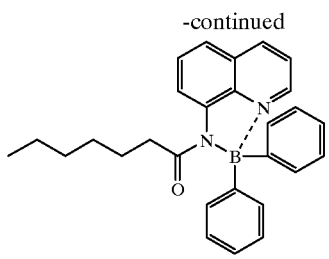

4.0 g (15.6 mmol) of the ligand from Example 1 and 5.4 g (15.6 mmol) of diphenylboric anhydride are refluxed in 250 ml of a dry mixture of ethanol/tetrahydrofuran (3:1) with TLC monitoring. Removal of the solvent gives a crude product which can be purified by chromatography.

This gives 2.1 g (≈32% of theory) of an orange solid which displays a green solid-state fluorescence. The compound is completely soluble in cold methanol.

Examples, Physical Part

Application Example 1

The substance B4 according to the invention is used for making an organic light emitting diode (OLED). The following procedure was used for producing the OLED:
1. Cleaning the ITO Substrate
    ITO-coated glass (Merck Balzers AG, FL, Part. No. 253 674 XO) is cut into 50 mm×50 mm pieces (substrates). The substrates are subsequently cleaned in a 3% strength aqueous Mukasol solution in an ultrasonic bath for 15 min. The substrates are then rinsed with distilled water and spun dry in a centrifuge. This rinsing and drying procedure is repeated 10 times.
2. Application of the ®Baytron P Layer to the ITO
    About 10 ml of the 1.3% strength polyethylenedioxythiophene/polystyrenesulphonic acid solution (Bayer AG, Baytron P) are filtered (Millipore HV, 0.45 μm). The substrate is subsequently placed on a spin coater and the filtered solution is spread over the ITO-coated side of the substrate. The excess solution on the substrate is subsequently spun off by rotation of the plate at 500 rpm for 3 minutes. The substrate which has been coated in this way is then dried at 110° C. for 5 minutes on a hotplate. The thickness of the layer is 60 nm (Tencor, Alphastep 200).
3. Application of the Hole Conduction Layer
    5 ml of a 1.5% strength dichloroethane solution of 1 part by weight of polyvinylcarbazole (BASF, Luvican), 1 part by weight of phenylamine (Agfa-Gevaert, Compound A1) and 1 part by weight of phenylamine (Agfa-Gevaert, A2) are filtered (Millipore HV, 0.45 μm) and spread on the dried Baytron P layer. The excess solution on the substrate is subsequently spun off by rotation of the plate at 800 rpm for 30 seconds. The substrate which has been coated in this way is then dried at 110° C. for 5 minutes on a hotplate. The total thickness of the layers is 150 nm.
4. Application of the Light-emitting Electron-injecting Layer by Vapour Deposition
    A third organic layer, namely the substance B4 according to the invention, is applied to the above two organic layers by thermal vapour deposition. This is carried out in a vapour deposition unit (Leybold, Univex 350). The pressure in the vapour deposition unit during the deposition procedure is $10^{-3}$ Pa and the deposition rate is 2 Å/sec. The total thickness of the 3 organic layers is 200 nm.
5. Application of the Metal Cathode by Vapour Deposition A metal electrode is applied to the organic layer system by vapour deposition. For this purpose, the substrate is placed with the organic layer system facing downwards on a perforated mask (hole diameter: 5 mm). At a pressure of $10^{-3}$ Pa, the elements Mg and Ag are vaporized in parallel from two vaporization boats. The deposition rate for Mg is 28 Å/sec. The thickness of the vapour-deposited metal contacts is 500 nm.

The two electrodes of the organic LED are connected to a voltage source by means of electric leads. The positive pole is connected to the ITO electrode and the negative pole is connected to the MgAg electrode.

From a voltage of only 3 volt, electroluminescence can be detected by means of a photodiode (EG&G C30809E). At a voltage of 10 volt, the current per unit area is 1.5 mA/cm² and the electroluminescence is readily visible. The colour of the electroluminescence is greenish blue.

What is claimed is:
1. An electroluminescent assembly comprising a substrate, an anode, an electroluminescent element, and a cathode, wherein

(1) at least one of the anode and/or cathode is transparent in the visible spectral region, and
(2) the electroluminescent element contains a boron complex of an 8-aminoquinoline derivative and consists of one or more zones selected from the group consisting of a hole injection zone, a hole transport zone, an electroluminescent zone, an electron transport zone, and an electron injection zone arranged in the order listed, with the proviso that each said zone can optionally assume functions of other such zones such that the electro-luminescent element as a whole exhibits hole-injecting, hole-transporting, electroluminescent, electron-transporting, and electron-injecting functions, wherein the hole injection zone must be present and contains
    (i) an uncharged or cationic polythiophene having the formula (I)

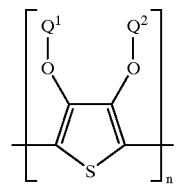

wherein
    $Q^1$ and $Q^2$ independently represent hydrogen or substituted or unsubstituted $(C_1–C_{20})$-alkyl, $CH_2OH$, or $(C_6–C_{14})$-aryl or
    $Q^1$ and $Q^2$ together represent $—(CH_2)_m—CH_2—$, wherein m is 0 to 12, or $(C_6–C_{14})$-arylene, and
    n represents an integer from 2 to 10,000, or
(ii) one or more uncharged or cationic polythiophenes of the formulas (Ia) and/or (Ib)

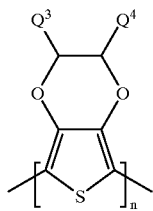

and/or

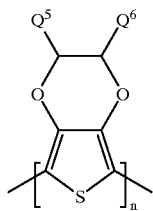

wherein
Q³ and Q⁴ independently represent hydrogen or a substituted or unsubstituted ($C_1$–$C_{18}$)-alkyl, ($C_2$–$C_{12}$)-alkenyl, ($C_3$–$C_7$)-cycloalkyl, ($C_7$–$C_{15}$)-aralkyl, ($C_6$–$C_{10}$)-aryl, ($C_1$–$C_{18}$)-alkyloxy, or ($C_2$–$C_{18}$)-alkyloxy ester group, Q⁵ and Q⁶ independently represent hydrogen or a ($C_1$–$C_{18}$)-alkyl, ($C_2$–$C_{12}$)-alkenyl, ($C_3$–$C_7$)-cycloalkyl, ($C_7$–$C_{15}$)-aralkyl, ($C_6$–$C_{10}$)-aryl, ($C_1$–$C_{18}$)-alkoxy, or ($C_2$–$C_{18}$)-alkyloxy ester group substituted by at least one sulphonate group, with the proviso that Q⁵ and Q⁶ cannot both be hydrogen, and n represents an integer from 2 to 10,000.

2. An electroluminescent assembly according to claim 1 wherein the hole injection zone contains one or more uncharged or cationic polythiophenes of the formulas (Ia-1) and/or (Ib-1)

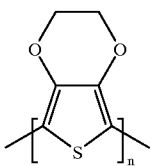

and/or

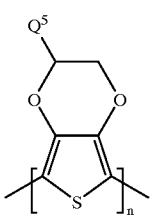

wherein
Q⁵ represents a ($C_1$–$C_{18}$)-alkyl, ($C_2$–$C_{12}$)-alkenyl, ($C_3$–$C_7$)-cycloalkyl, ($C_7$–$C_{15}$)-aralkyl, ($C_6$–$C_{10}$)-aryl, ($C_1$–$C_{18}$)-alkoxy, or ($C_2$–$C_{18}$)-alkyloxy ester group substituted by at least one sulphonate group, and n represents an integer from 2 to 10,000.

3. An electroluminescent assembly according to claim 1 additionally comprising polyanions selected from the group consisting of polymeric carboxylic acids, polymeric sulphonic acids, and mixtures thereof in the hole injection zone.

4. An electroluminescent assembly according to claim 1 additionally comprising counterions selected from the group consisting of polystyrene sulphonic acids, alkaline earth metal salts, and mixtures thereof in the hole injection zone.

5. An electroluminescent assembly according to claim 1 wherein the hole injection zone and/or the hole transport zone contains an aromatic tertiary amino compound having the formula (II)

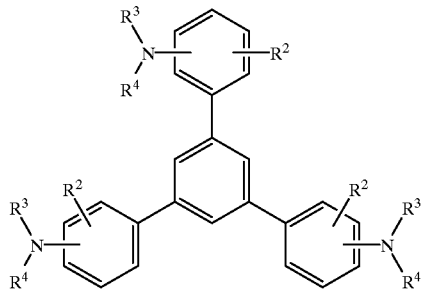

wherein
R² represents hydrogen, substituted or unsubstituted alkyl, or halogen, and
R³ and R⁴ independently represent substituted or unsubstituted ($C_1$–$C_{10}$)-alkyl, alkoxycarbonyl-substituted ($C_1$–$C_{10}$)-alkyl, or substituted or unsubstituted aryl, aralkyl, or cycloalkyl.

6. An electroluminescent assembly according to claim 1 wherein the hole injection zone and/or the hole transport zone contains an aromatic tertiary amino compound having the formula (II)

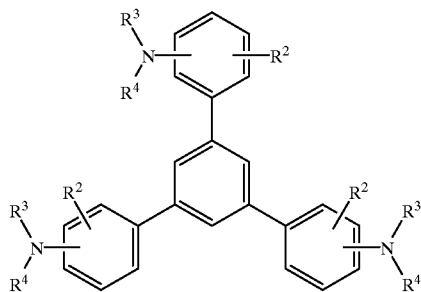

wherein
R² represents hydrogen or ($C_1$–$C_6$)-alkyl, and R³ and R⁴ independently represent ($C_1$–$C_6$)-alkyl, ($C_1$–$C_4$)-alkoxycarbonyl-($C_1$–$C_6$)-alkyl, unsubstituted phenyl, naphthyl, phenyl-($C_1$–$C_4$)-alkyl, naphthyl-($C_1$–$C_4$)-alkyl, cyclopentyl, or cyclohexyl, ($C_1$–$C_4$)-alkyl-substituted phenyl, naphthyl, phenyl-($C_1$–$C_4$)-alkyl, naphthyl-($C_1$–$C_4$)-alkyl, cyclopentyl, or cyclohexyl, or ($C_1$–$C_4$)-alkoxy-substituted phenyl, naphthyl, phenyl-($C_1$–$C_4$)-alkyl, naphthyl-($C_1$–$C_4$)-alkyl, cyclopentyl, or cyclohexyl.

7. An electroluminescent assembly according to claim 1 wherein the hole injection zone and/or the hole transport zone contains one or more aromatic tertiary amino compounds selected from the group consisting of compounds having the formulas
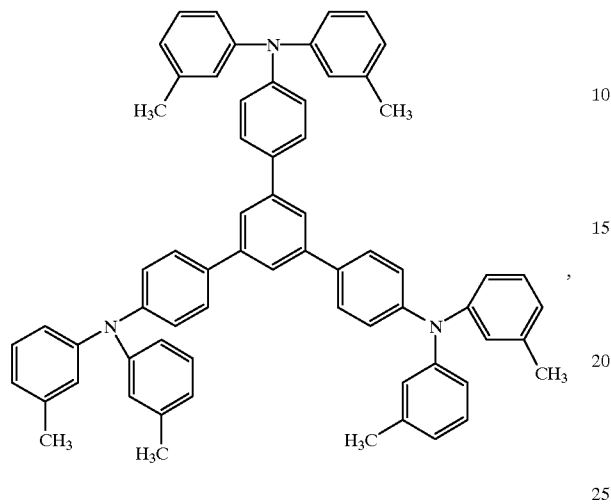
,
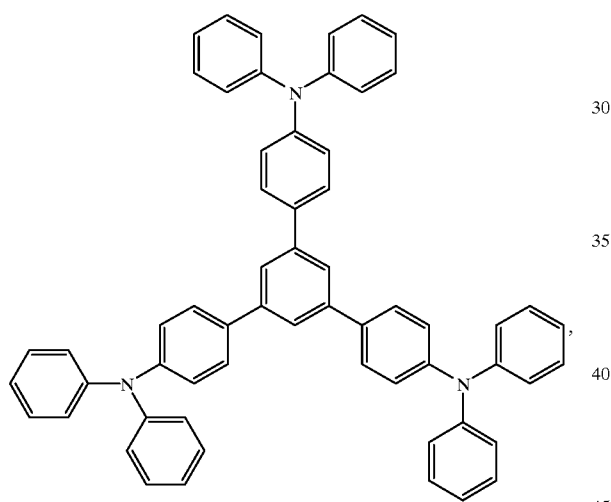
,
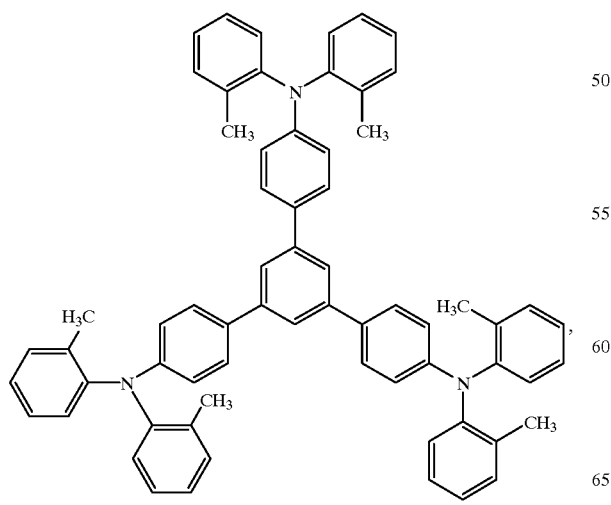
,
-continued
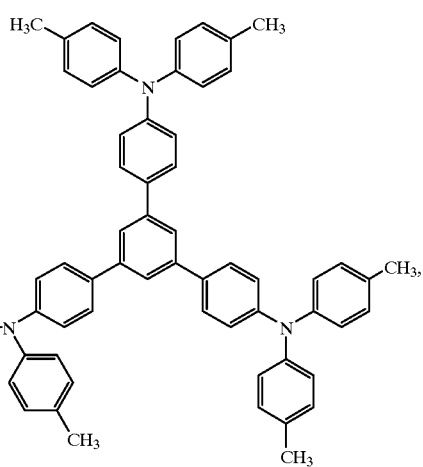
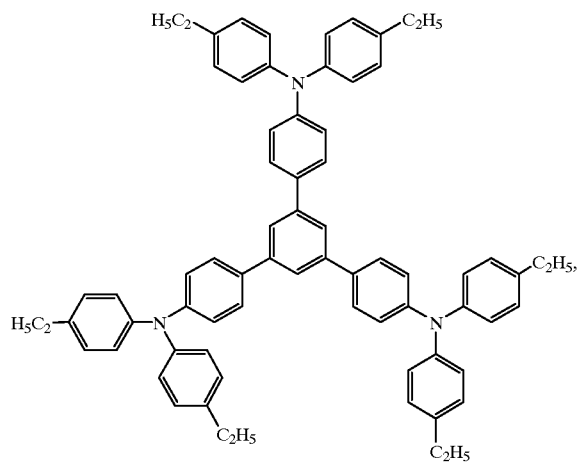

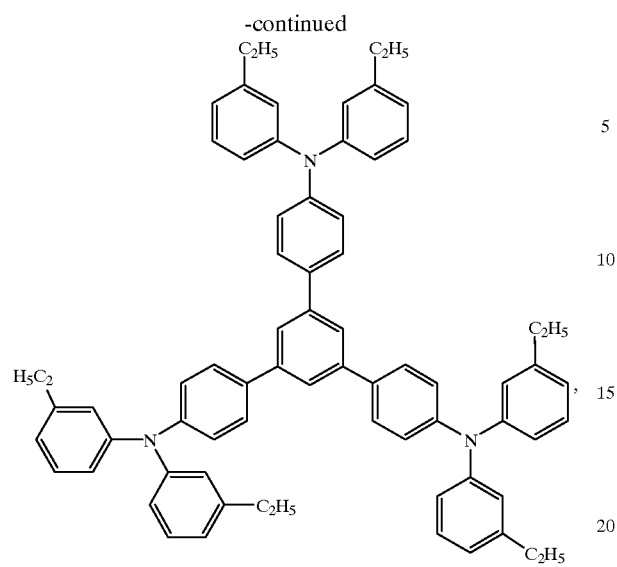
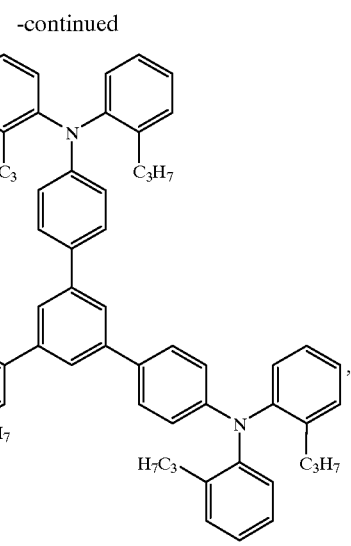
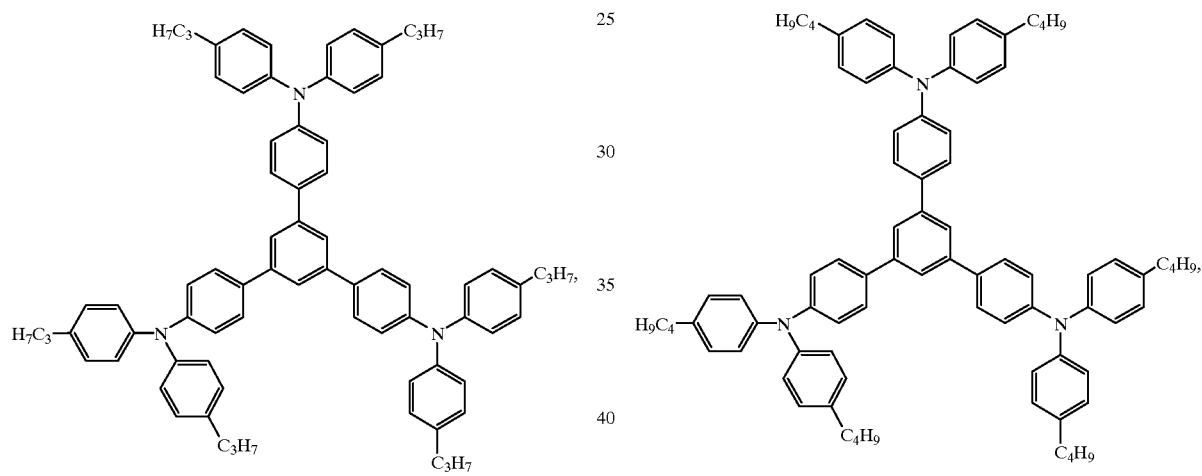
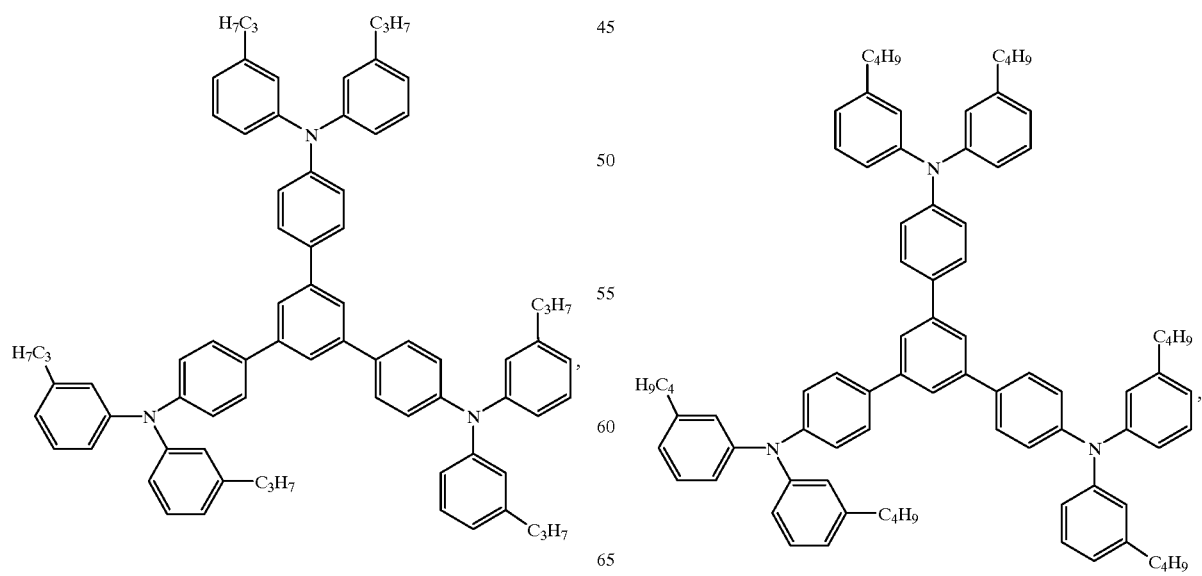

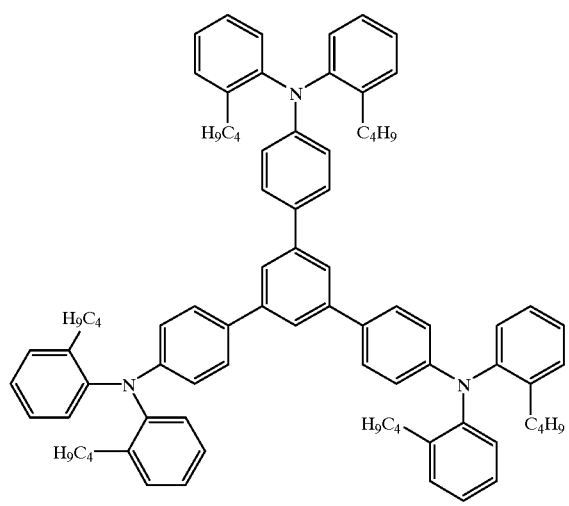
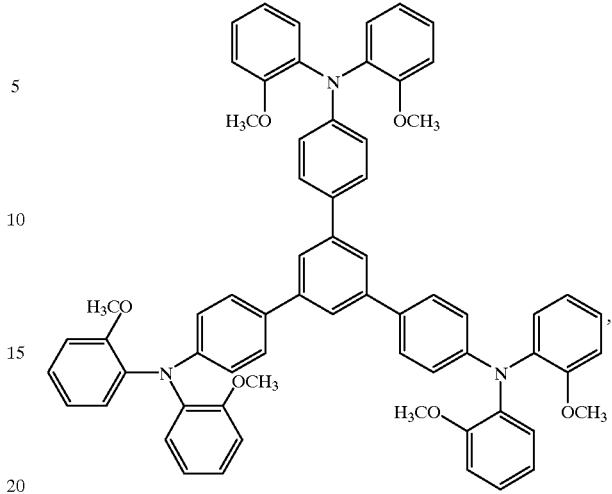
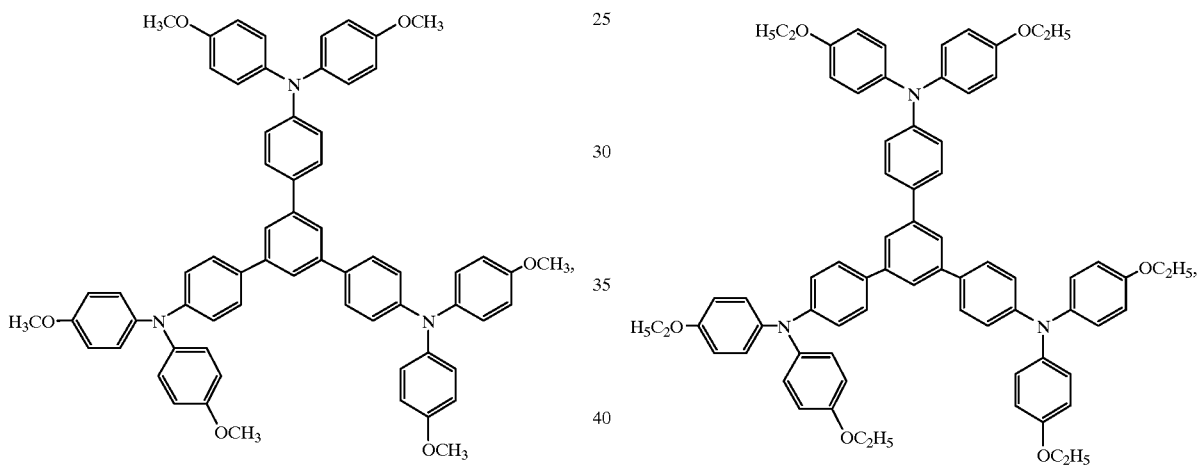
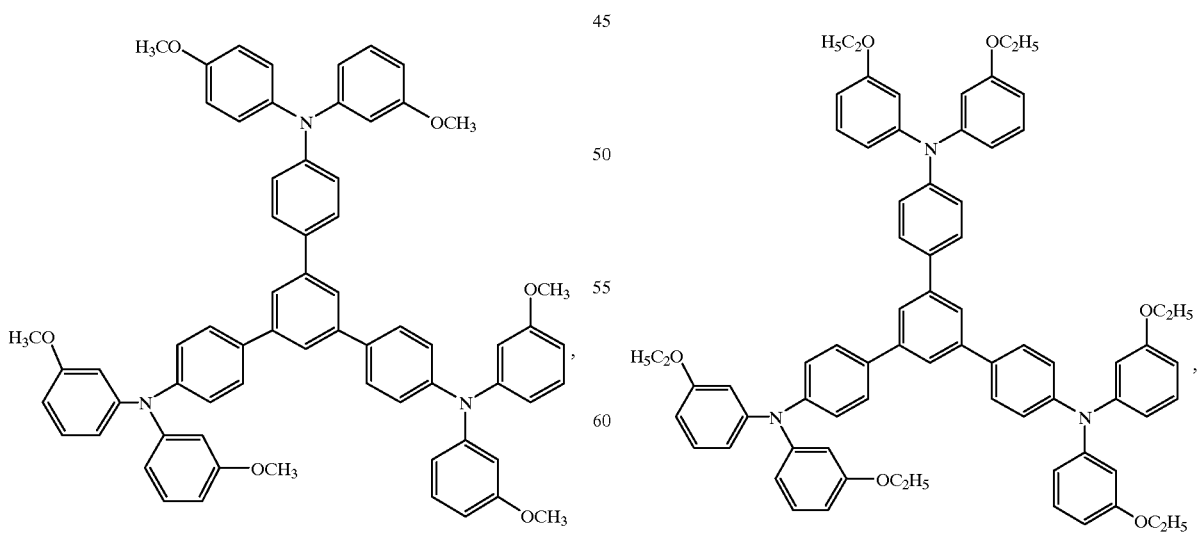

-continued
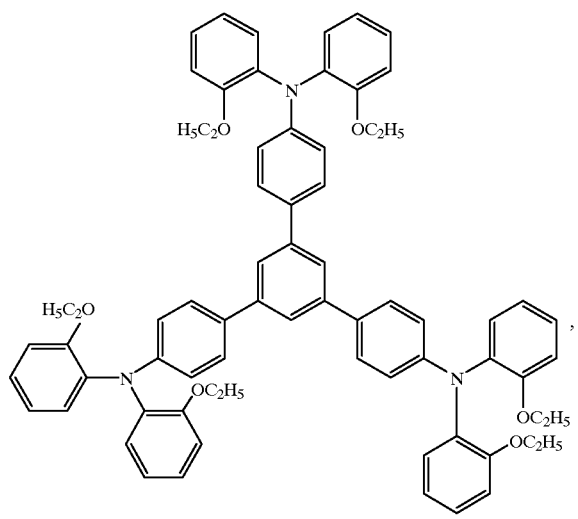
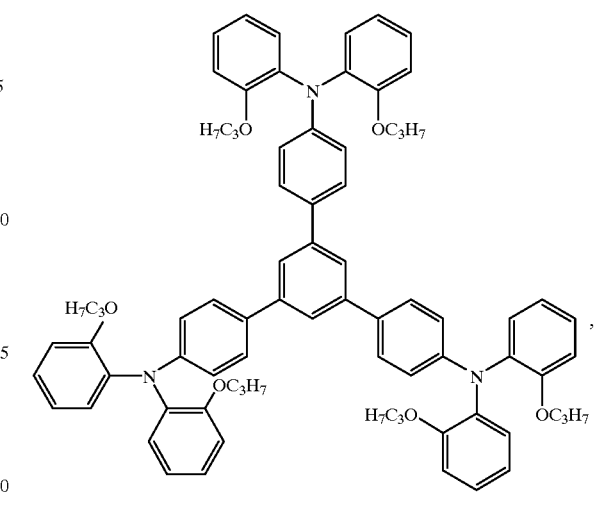
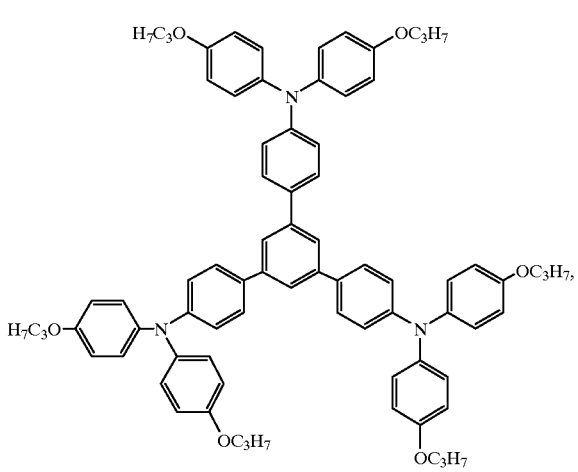
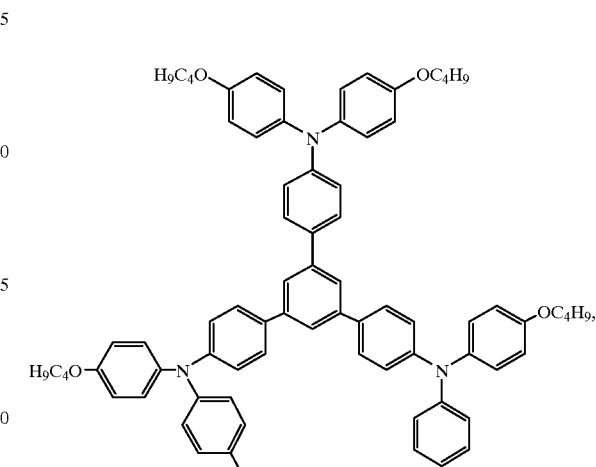
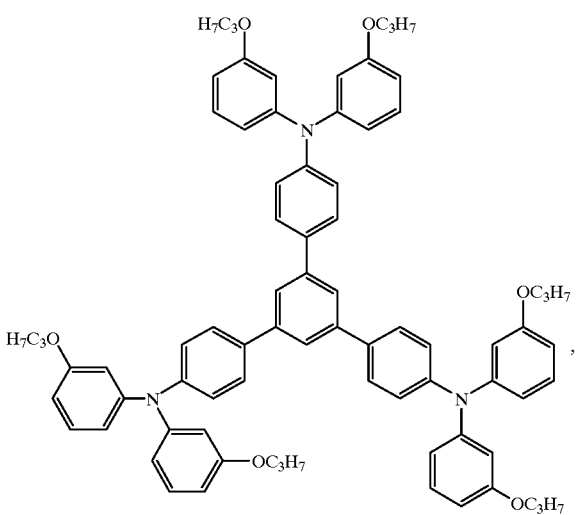
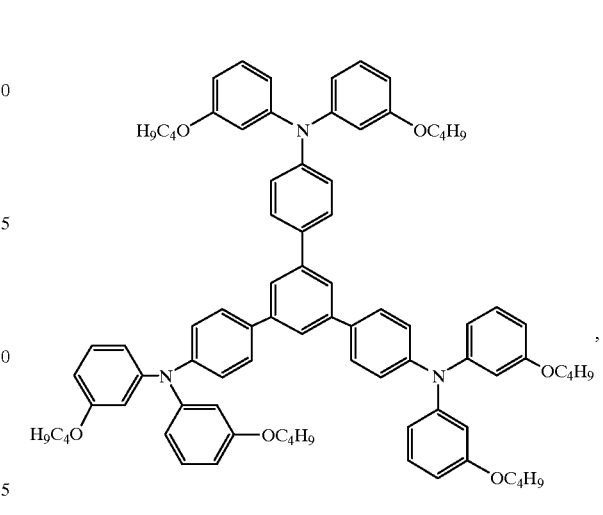

35
-continued
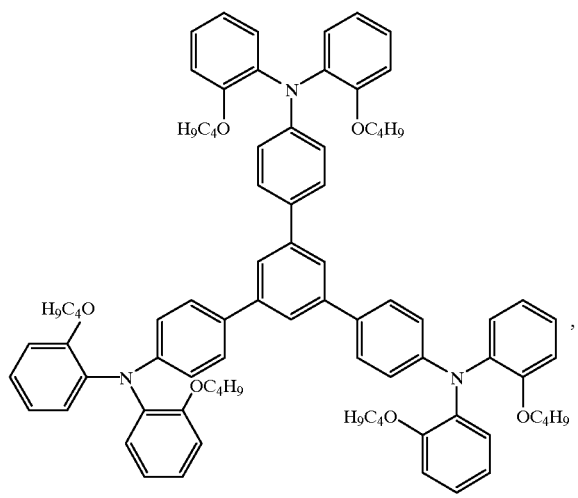
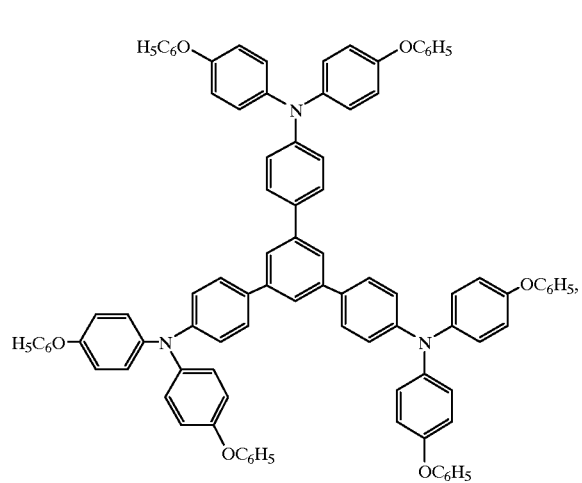
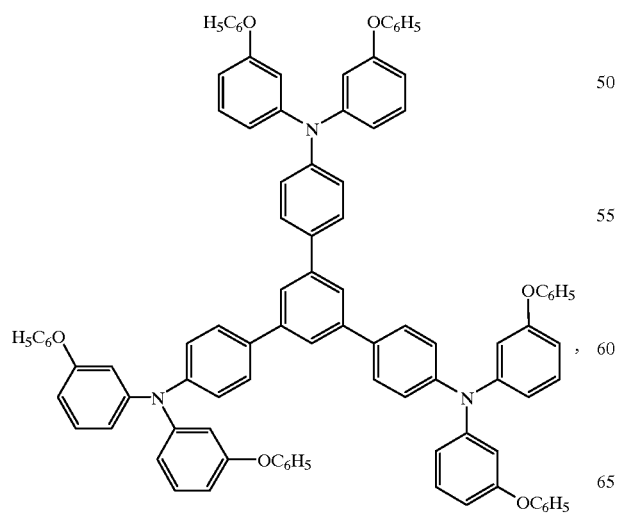
36
-continued
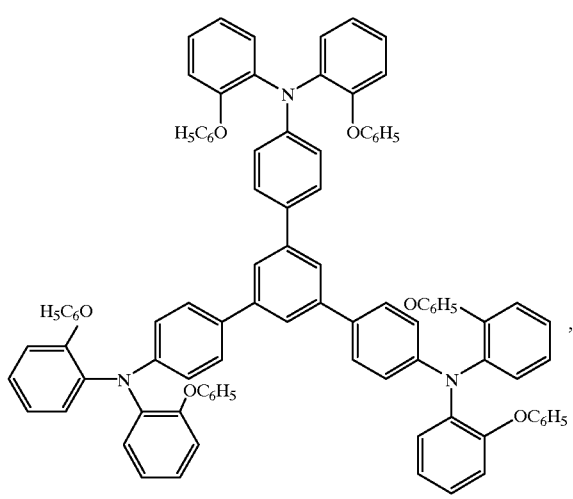
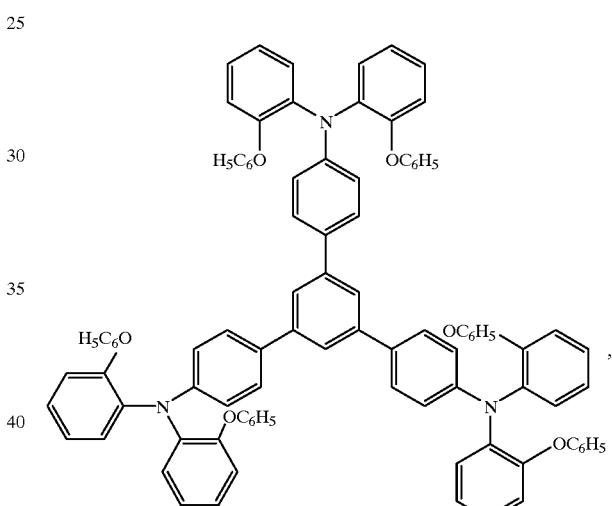
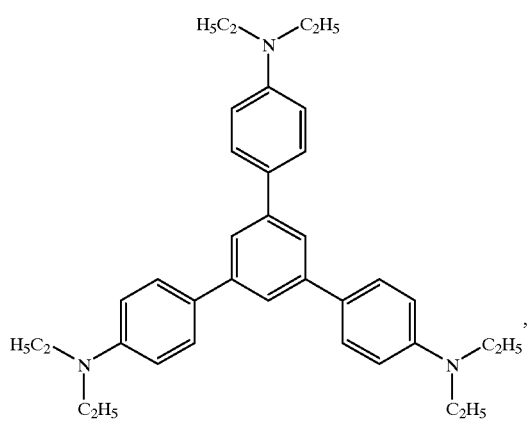

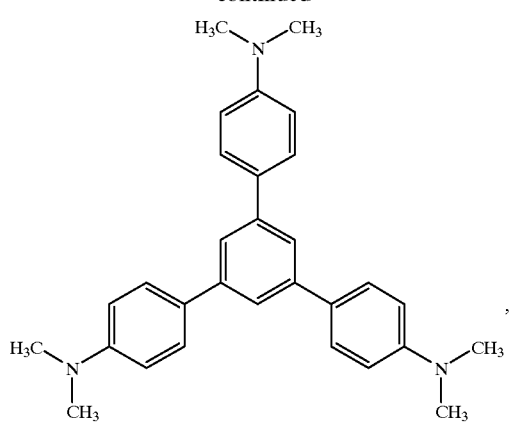
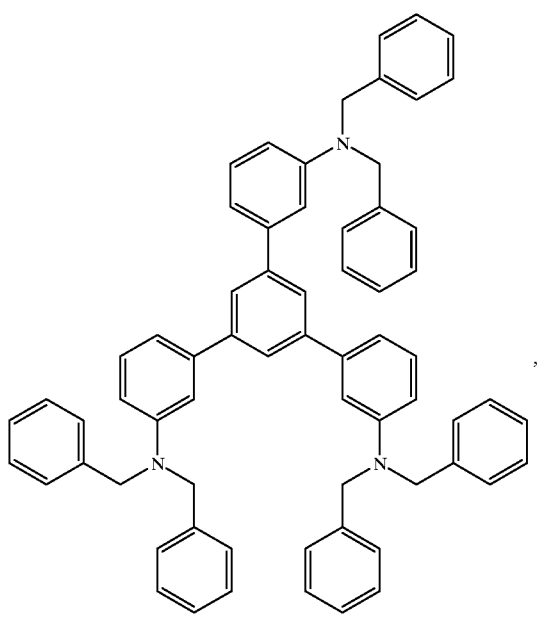
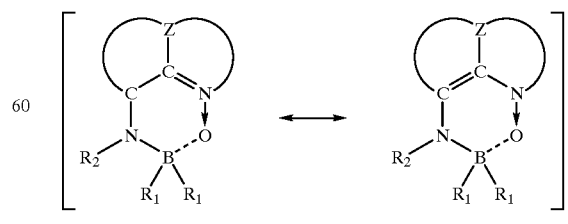
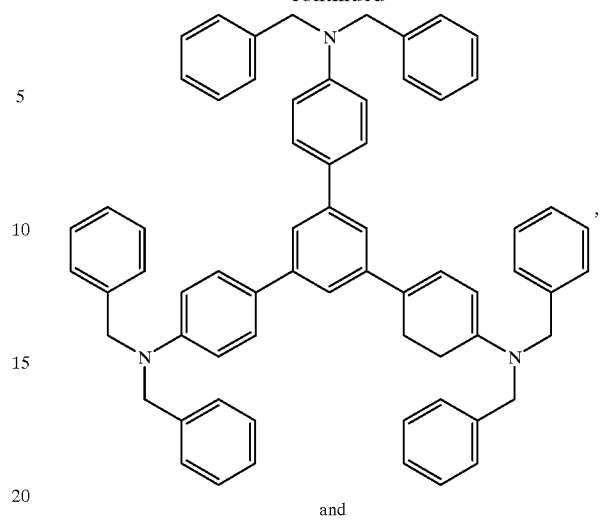
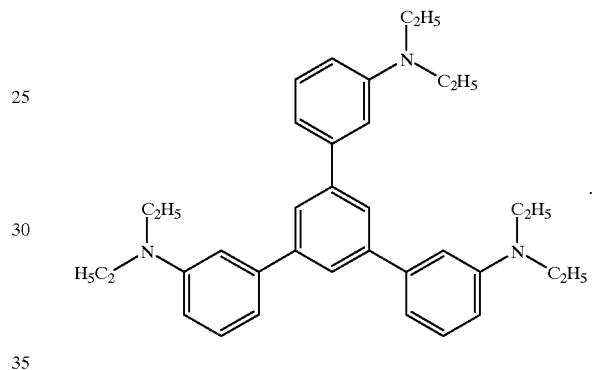
8. An electroluminescent assembly according to claim 1 wherein the boron complex of an 8-aminoquinoline derivative is one or more compounds having the formulas (III)a and/or (III)b
(III)a
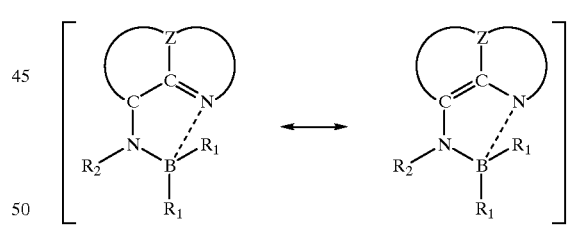
and/or
(III)b
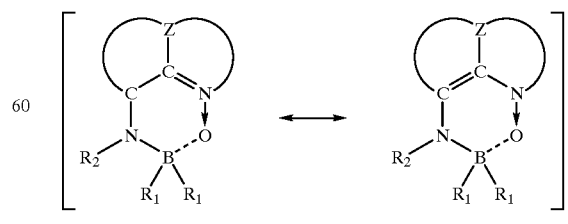

wherein

R¹ represents a substituted or unsubstituted aryl radical or fluorine,

R² represents a substituted or unsubstituted aryl or acyloxy radical or hydrogen, and Z represents atoms that complete a ring system having at least two fused rings.

9. An electroluminescent assembly according to claim 1 wherein the boron complex of an 8-aminoquinoline derivative is one or more compounds having the formulas (III)c and/or (III)d

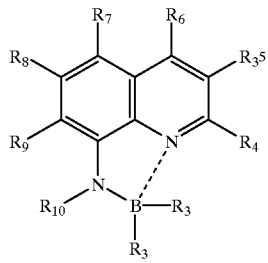
(III)c and/or

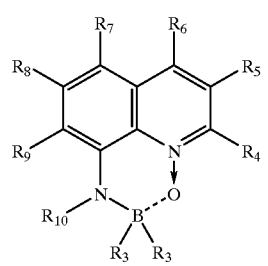
(III)d wherein $R_3$ represents substituted or unsubstituted $(C_6-C_{10})$-aryl or halogen, $R_4$, $R_5$, $R_6$, $R_7$, $R_8$, and $R_9$ independently represent hydrogen, substituted or unsubstituted $(C_1-C_{16})$-alkyl, halogen, a sulfonamide, cyano, or a substituted or unsubstituted amino group, and $R_{10}$ represents a substituted or unsubstituted acyl or acyloxy radical.

10. An electroluminescent assembly according to claim 1 wherein the boron complex of an 8-aminoquinoline derivative is one or more compounds having the formulas

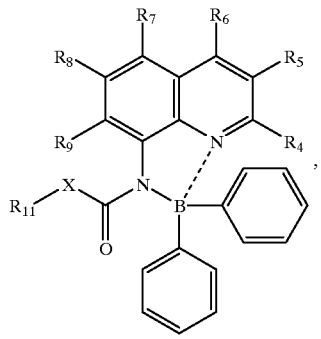
(III)e

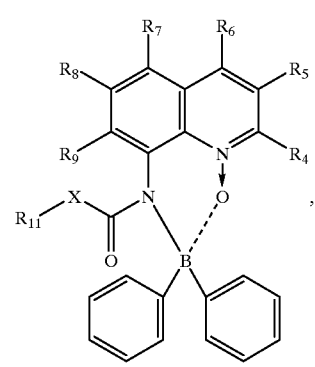
(III)f and/or

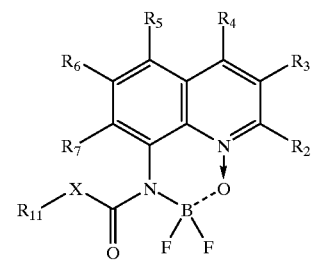
(III)g wherein
$R_4$, $R_5$, $R_6$, R7, $R_8$, and $R_9$ independently represent hydrogen, branched or unbranched $(C_1-C_{12})$-alkyl, chlorine, a sulfonamide, cyano, or a substituted amino group, $R_{11}$ represents a substituted or unsubstituted branched or unbranched alkyl, and X represents an O atom or a —$CH_2$— or —NH—group.

11. An electroluminescent assembly according to claim 1 additionally containing one or more transparent binders selected from the group consisting of polycarbonates, polyester carbonates, copolymers of styrene, polysulphones, polymers based on vinyl-containing monomers, polyolefins, cyclic olefin copolymers, and phenoxy resins.

12. An electroluminescent assembly according to claim 1 wherein the boron complex of an 8-aminoquinoline derivative is selected from the group consisting of compounds having the formulas

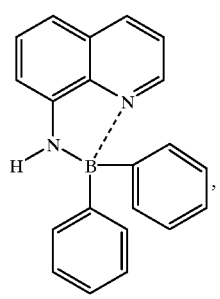
B1)
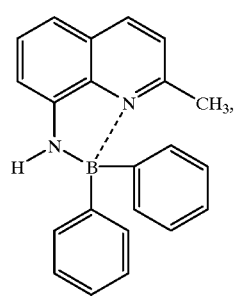
B2)
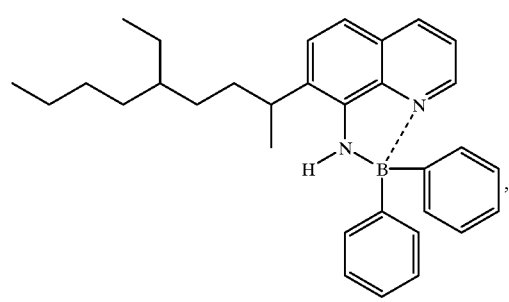
B3)
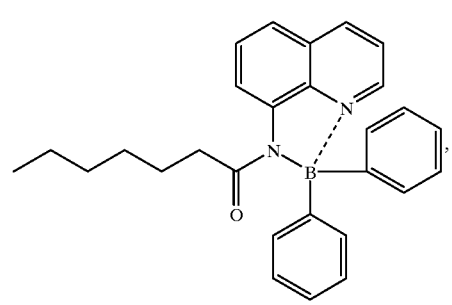
B4)
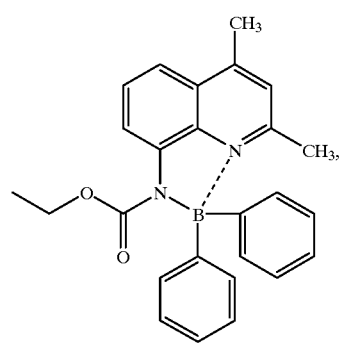
B5)
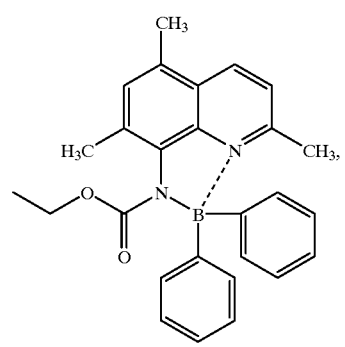
B6)
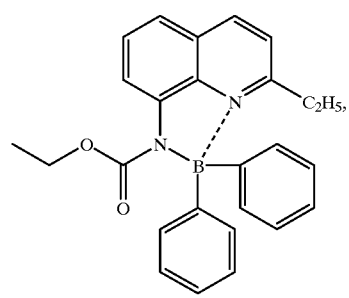
B7)
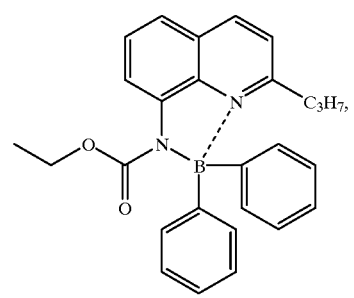
B8)

B9) 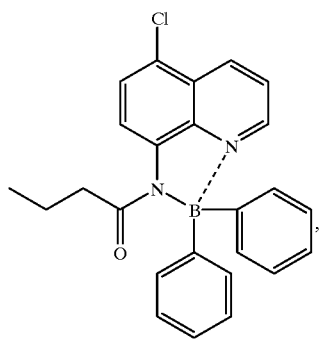
B10) 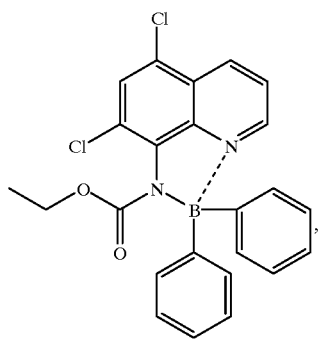
B11) 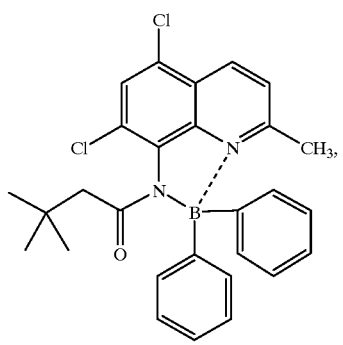
B12) 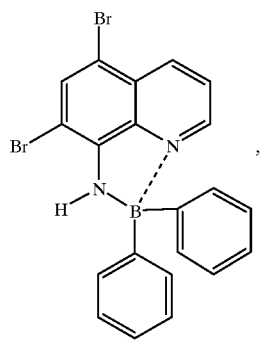
B13) 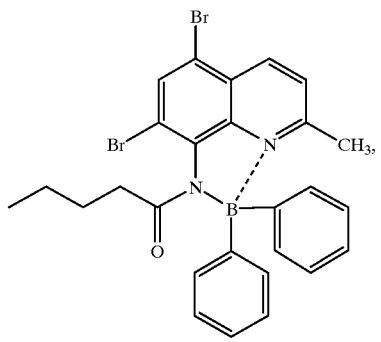
B14) 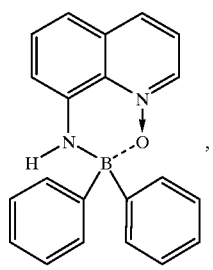
B15) 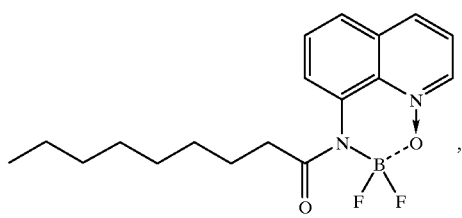
B16) 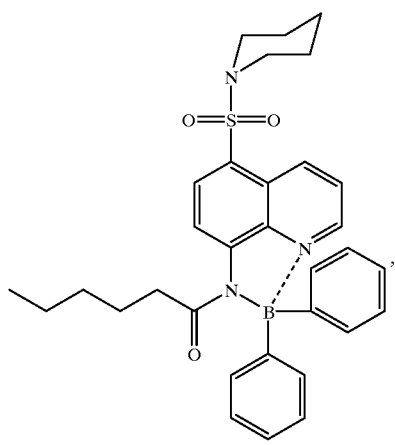

-continued
B17)
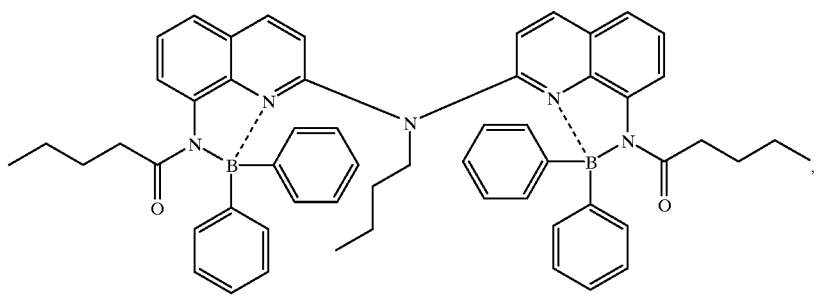
B18)
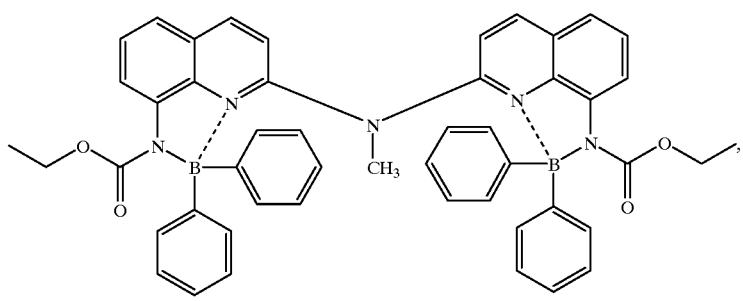
B19)
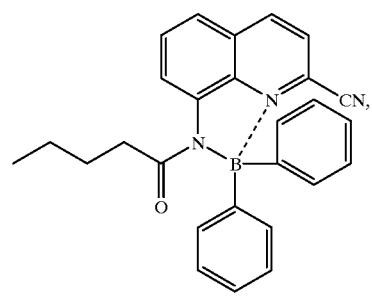
B20)
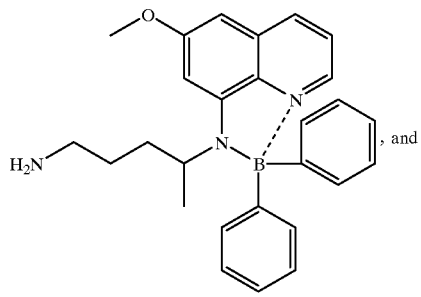, and
B21)
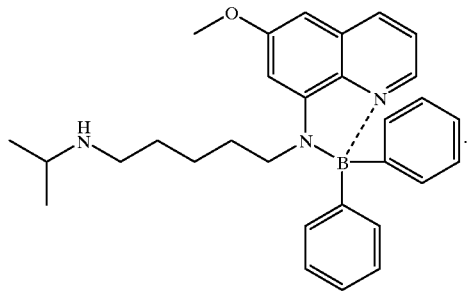
* * * * *